(12) United States Patent
MacDonald et al.

(10) Patent No.: US 11,344,747 B2
(45) Date of Patent: May 31, 2022

(54) COORDINATED RADIOTHERAPY FOR PLURAL TARGETS

(71) Applicant: Dalhousie University, Halifax (CA)

(72) Inventors: Robert Lee MacDonald, Antigonish (CA); Alasdair Syme, Halifax (CA); Christopher G. Thomas, Halifax (CA)

(73) Assignee: Dalhousie University, Halifax (CA)

( * ) Notice: Subject to any disclaimer, the term of this patent is extended or adjusted under 35 U.S.C. 154(b) by 211 days.

(21) Appl. No.: 16/615,074

(22) PCT Filed: May 24, 2018

(86) PCT No.: PCT/CA2018/050609
§ 371 (c)(1),
(2) Date: Nov. 19, 2019

(87) PCT Pub. No.: WO2018/213930
PCT Pub. Date: Nov. 29, 2018

(65) Prior Publication Data
US 2020/0164227 A1    May 28, 2020

Related U.S. Application Data

(60) Provisional application No. 62/510,689, filed on May 24, 2017.

(51) Int. Cl.
*A61N 5/10* (2006.01)
(52) U.S. Cl.
CPC ......... *A61N 5/1036* (2013.01); *A61N 5/1047* (2013.01); *A61N 5/1071* (2013.01)

(58) Field of Classification Search
CPC ........ A61N 5/10; A61N 5/103; A61N 5/1031; A61N 5/1036; A61N 5/1042;
(Continued)

(56) References Cited

U.S. PATENT DOCUMENTS

| 8,913,717 B2 | 12/2014 | Siljamaki et al. |
| 2013/0142310 A1 | 6/2013 | Fahimian et al. |
| 2018/0154179 A1* | 6/2018 | Ollila ................... A61N 5/1065 |

FOREIGN PATENT DOCUMENTS

| WO | 2013075743 A1 | 5/2013 |
| WO | 2015039903 A1 | 3/2015 |

(Continued)

OTHER PUBLICATIONS

Cerny, V. et al., "Thermodynamical Approach to the Traveling Salesman Problem: An Efficient Simulation Algorithm", Journal of Optimization Theory and Applications, vol. 45, No. 1, Jan. 1985.

(Continued)

*Primary Examiner* — Anastasia Midkiff
(74) *Attorney, Agent, or Firm* — Oyen Wiggs Green & Mutala LLP

(57) ABSTRACT

A radiation treatment planning system and method for generating plans to treat plural target volumes, each associated with a prescribed dose, does not require delivery of radiation to every target volume from every beam direction. Allowing target volumes to be omitted for some control points facilitates generation of treatment plans that deliver less radiation dose to non-target tissues by allowing beam shaping to more closely fit the remaining target volumes. Simulated annealing using an objective function may be applied to determine parameters such as the number of control points for which a target volume is not targeted.

46 Claims, 17 Drawing Sheets

(58) Field of Classification Search
CPC .. A61N 5/1045; A61N 5/1048; A61N 5/1064; A61N 5/1065; A61N 5/1067; A61N 5/1071; A61N 5/1077; A61N 5/1081; A61N 5/1083; A61N 2005/1074; A61B 6/06; A61B 34/10; A61B 34/20; A61B 2034/107; G21K 1/00; G21K 1/02; G21K 1/04; G21K 1/046; G21K 5/00; G21K 5/04; G21K 5/10

See application file for complete search history.

(56) References Cited

FOREIGN PATENT DOCUMENTS

| | | |
|---|---|---|
| WO | 2016008052 A1 | 1/2016 |
| WO | 2017152286 A1 | 9/2017 |

OTHER PUBLICATIONS

Kirkpatrick, S. et al., "Optimization by Simulated Annealing", Science, vol. 220, No. 4598, May 1983, pp. 671-680.

* cited by examiner

- Met 1 & Met 2 & Met 3

○ Met 2 & Met 3

△ Met 1 & Met 3

∗ Met 3

FIG. 5F

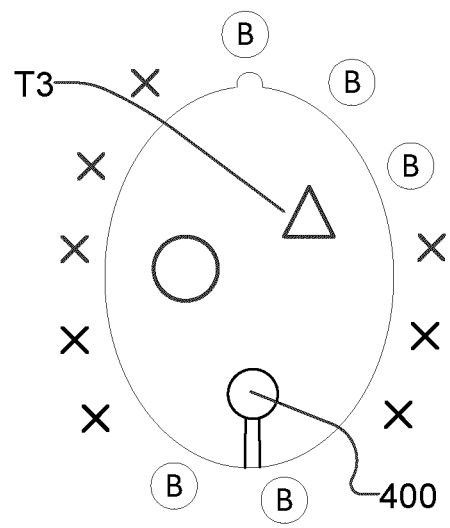
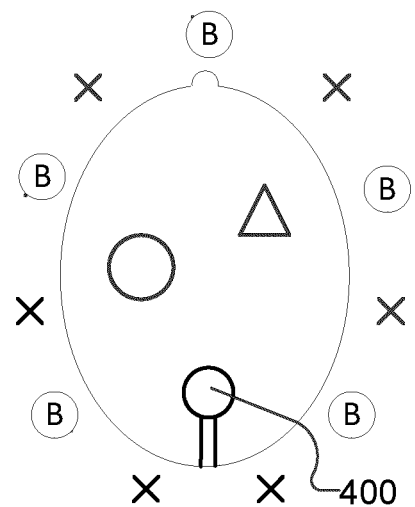
FIG. 6A  FIG. 6B
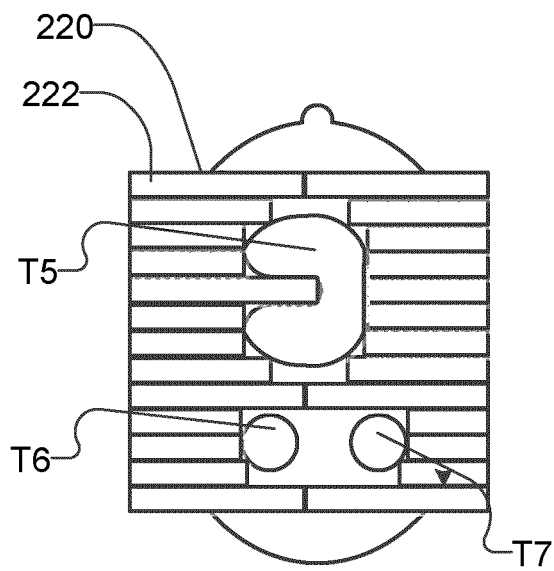
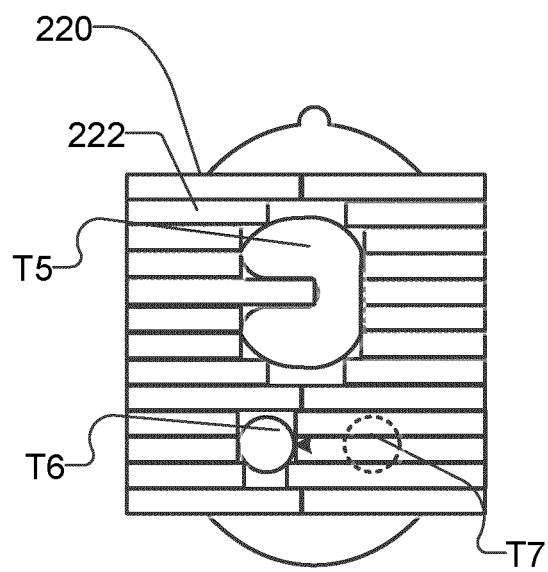
FIG. 7A  FIG. 7B

US 11,344,747 B2

COORDINATED RADIOTHERAPY FOR PLURAL TARGETS

CROSS-REFERENCE TO RELATED APPLICATIONS

This application claims priority from U.S. application No. 62/510,689 filed 24 May 2017. For purposes of the United States, this application claims the benefit under 35 U.S.C. § 119 of U.S. application No. 62/510,689 filed 24 May 2017 and entitled COORDINATED RADIOTHERAPY FOR PLURAL TARGETS which is hereby incorporated herein by reference for all purposes.

FIELD

The present disclosure relates to radiotherapy systems and methods. Some embodiments provide systems and methods useful in planning and/or delivering radiotherapy by arc therapy.

BACKGROUND

Radiotherapy involves delivering radiation to a subject. A non-limiting example application of radiotherapy is cancer treatment. Radiotherapy is widely used for treating tumors in the brain, for example. The radiation used for radiotherapy may comprise photon beams (e.g. x-rays) or particle beams (e.g. proton beams). Radiation for treatment of cancers and other conditions may, for example, be generated by a linear accelerator.

Ideally a radiotherapy treatment could deliver a prescribed radiation dose to a target volume (e.g. a brain tumor) while delivering no radiation outside of the target volume. This is not possible, in general, because the radiation beams used for radiotherapy must typically pass through overlying tissues to reach a target volume. The radiation beams deliver radiation dose to these overlying tissues as they pass through. Further, the radiation beams are not extinguished in the target volume. The radiation beams pass through the target volume and deliver dose to tissues on the side of the target volume away from the radiation source. Scattering of radiation from a radiation beam is another mechanism by which radiation dose is delivered outside of a target volume.

Although it is impossible to avoid delivering radiation dose to tissues outside of a target volume, the amount of dose delivered outside of the target volume and the way in which that dose is distributed in non-target tissues can be affected very significantly by how the radiation is delivered to the target volume. For example, a target volume may be irradiated by radiation beams incident from many directions which collectively deliver a prescribed dose to the target volume. This may result in relatively low doses to tissue outside of the target volume while achieving a distribution of dose within the target volume that more accurately matches a prescription (for example, the prescription may call for a specified uniform dose within the target volume).

The field of radiation treatment planning has been and remains the subject of a large amount of active research. This research has yielded various approaches to planning and delivering radiotherapy.

Arc therapies are a class of radiotherapy which involve moving a radiation source along a treatment trajectory (typically an arc) extending at least part way around a patient. Radiation doses are delivered to a target volume from locations on the trajectory. In some arc therapies, radiation is delivered continuously or substantially continuously as the radiation source is moved along the trajectory. By irradiating target volumes from a variety of angles, arc therapies aim to achieve the prescription doses assigned to planning target volumes while limiting the radiation exposure to healthy normal tissue and any sensitive structures.

Conformal arc therapies involve shaping a radiation beam (for example a cone beam), such that a cross-section of the beam is shaped to conform with the projection of the target volume in the beam's-eye-view (i.e. a view taken along a central axis of the radiation beam, abbreviated as BEV). Beam shaping is typically achieved by passing the beam through a beam shaper having an aperture that can be adjusted to conform at least roughly to the shape of the projection of the target volume. Deviations between the shape of the aperture and the boundary of the projection of the target volume are another source of dose to non-target tissues and/or deviations from prescribed dose within the target volume.

One type of beam shaper is a multiple leaf collimator (MLC). A MLC has two sets of leaves that can be advanced or retracted from either side of an opening to define a desired aperture. In some treatment modalities, positions of the leaves of a MLC are adjusted dynamically to change the shaping of a radiation beam as the beam source is moved along a trajectory.

For target volumes having certain shapes, the degree to which a radiation beam can be shaped by the leaves of a MLC to match the shape of the projection of the target volume can depend on the relative orientations of the target volume and the MLC leaves. Some arc therapy modalities that apply a MLC allow the MLC to be rotated to optimize beam shaping to match the projection of a target volume for different points along the trajectory. Arc therapies include, but are not limited to, dynamic conformal arcs and volumetric modulated arc therapy.

One type of arc therapy is intensity modulated arc therapy (IMAT). IMAT involves modulating the intensity of a radiation field. The intensity modulation can be controlled (for example, using a MLC) to improve conformation of a delivered dose distribution to a prescribed dose distribution.

In general, beam shapers, including MLCs, cannot completely block parts of a radiation beam. Radiation that leaks through the beam shaper outside of the aperture (e.g. though MLC leaves or through the joints between MLC leaves) can deliver non-negligible doses to non-targeted tissues.

Some non-target tissues may be more sensitive to radiation exposure and/or critical than others. Such non-targeted tissue may be called an organ-at-risk (OAR). It can be desirable to minimize dose delivered to OARs. For example, in delivering radiation to locations within a patient's brain, it is generally desirable to minimize dose delivered to the patient's optic nerves and brainstem, each of which may be considered to be an OAR in at least some applications.

FIG. 1 shows an example radiotherapy system 100 of a type that may be used for performing radiotherapy. The example system includes a gantry 102, which houses a radiation source (e.g. a linear accelerator) that can be controlled to emit a radiation beam 110 toward patient P. Gantry 100 may include motors to rotate the gantry, and thereby rotate the point of origin of radiation beam 110 in an arc around patient P. Radiotherapy systems that are generally like system 100 are commercially available from companies such as Varian and Elekta.

FIG. 2 shows an example beam shaper 200 that includes a jaw system 210 and a MLC 220. Jaw system 210 comprises two sets of orthogonally positioned jaws 210A and 210B (only one of jaws 210B is shown in FIG. 2). Jaws of sets 210A and 210B may be positioned to shape the radiation beam into a rectangular shape. MLC 220 comprises two banks 220A and 220B of collimator leaves 222. Corresponding ones of leaves 222 from banks 220A and 220B may be advanced toward one another or retracted away from one another. Each of collimator leaves 222 may be independently positioned to shape the aperture through which the radiation beam will pass.

A wide range of approaches to radiation treatment planning have been discussed in the academic and patent literature. Commercially available radiation treatment planning systems implement some of these approaches. While some of these approaches can yield dose distributions that are close to the best that can be achieved for certain geometries of target volumes, there remains a need for approaches that can yield better dose distributions for other geometries.

SUMMARY

This invention has a number of aspects. These include, without limitation:
  Radiation treatment planning apparatus and methods;
  Apparatus and methods for controlling radiotherapy apparatus such as medical linear accelerator systems; and
  Apparatus and methods for delivering radiation treatments.

Certain aspects of the invention relate to cases where there are a plurality of target volumes and at least some of the target volumes have been prescribed different doses. In such cases, inventive methods and apparatus as described herein may avoid targeting one or more lower-dose target volumes for one or more possible beam directions (e.g. for one or more points or areas along an arc therapy trajectory).

According to some aspects of the invention, planning radiation treatment to deliver radiation to specified target volumes involves determining a configuration for a beam shaper (e.g. a MLC) at selected control points along a trajectory. The configuration may be based at least in part on the shapes and locations of the target volumes in a beam's-eye-view corresponding to the control point. These shapes and locations may be determined from imaging of the patient (e.g. computed tomography (CT) and/or magnetic resonance imaging (MRI)). Determining the configuration for the beam shaper may attempt to define an aperture that follows boundaries of the projections of the target volumes closely. Methods and apparatus may omit one or more of the target volumes from one or more of the control points. This may facilitate finding and/or providing a configuration of the beam shaper that provides an aperture that better fits to the perimeters of the projections of the remaining target volumes.

Another aspect of the invention provides apparatus and computer-implemented optimization processes for planning the amount of radiation to be delivered at different points along a trajectory and/or controlling a radiotherapy apparatus to deliver radiation. The optimization process may apply an objective function and penalty function based on a variety of quantifiable metrics.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIGS. 5A-5E show example target blinking schedules and FIG. 5F is a legend to show which targets are considered at each control point in the examples of FIGS. 5A to 5E.

FIGS. 6A and 6B illustrate example ways to distribute control points where a target volume is and is not taken into account for beam shaping.

FIG. 7A shows an example MLC configuration defining an aperture that includes all of a plurality of target volumes.

FIG. 7B shows an example MLC configuration defining an aperture that omits one of the target volumes.

DETAILED DESCRIPTION

Figure 1:
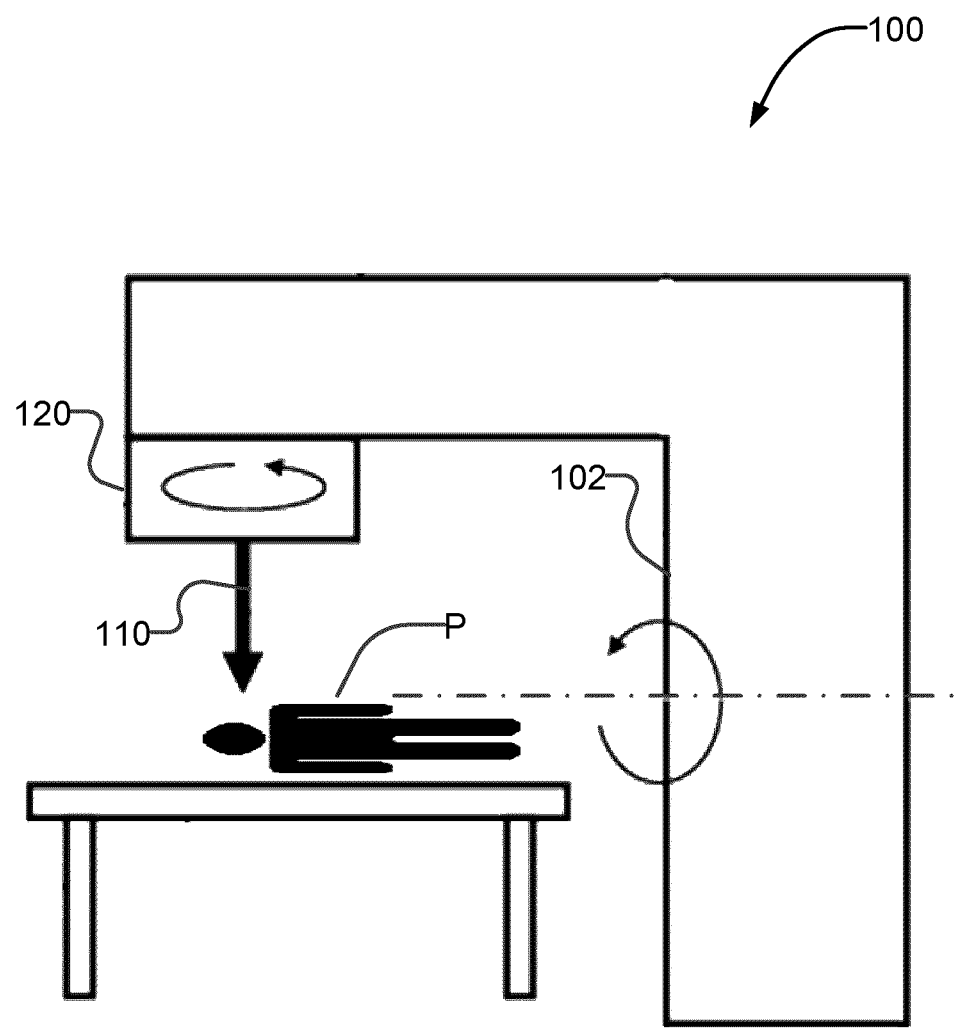
FIG. 1 is a schematic illustration showing an example prior art radiation treatment system.
Figure 2:
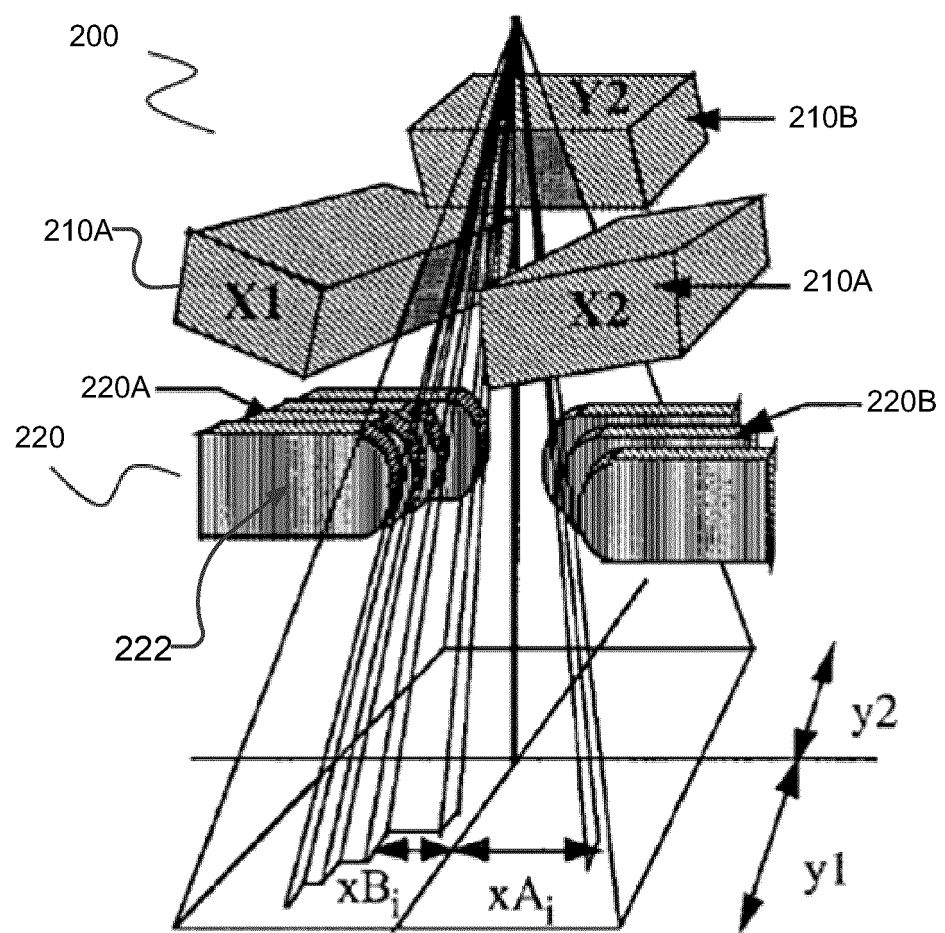
FIG. 2 is a schematic illustration showing an example prior art beam shaper that includes a multileaf collimator.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Some radiotherapy treatment scenarios require radiation to be delivered to two or more target volumes (two or more brain tumors as a non-limiting example). Different ones of the targets may have different prescribed doses. For example, a prescription may specify a dose of 100 units in one target volume and a dose of 50 units for another target volume. Radiation treatment planning is complicated in such scenarios by the goal of providing the prescription dose assigned to each target volume and the difficulty of shaping a radiation beam to irradiate plural target volumes without delivering excessive dose to tissues outside of the target volumes.

In some embodiments of the present invention, one or more lower-dose target volumes are selectively omitted from consideration for certain points or areas along an arc therapy trajectory. In some cases this can provide significant benefits such as:
  treatment plans resulting in lower dose to non-target tissues;
  treatment plans resulting in lower dose to organs-at-risk; and/or
  treatment plans which permit greater flexibility in optimizing the rates at which radiation may be delivered at different points on a trajectory.

Different implementations apply different approaches to determining which target volumes to be omitted from consideration for which parts of a trajectory.

A radiation treatment plan specifies a set of parameters that define how radiation will be delivered to a patient. For example, a radiation treatment plan may specify some or all of:
- a trajectory to be followed by a radiation source relative to a patient;
- a rate at which the trajectory is followed;
- how a radiation beam is shaped at different points along the trajectory;
- the intensity or other characteristics of the radiation beam.

In some cases one or more parameters may be static (i.e. they do not change in the course of delivering the planned treatment). In other cases one or more parameters may change dynamically as the treatment is delivered.

A trajectory may define motion of a radiation source relative to a fixed patient, motion of a patient relative to a fixed radiation source or motions of both patient and a radiation source. A trajectory may be simple, such as motion of a radiation source in an arc, or more complicated, such as coordinated motions of both a radiation source and a couch or other patient support. A trajectory may include plural parts. For example a trajectory may comprise plural arcs. A non-limiting example of a trajectory is a 4 arc trajectory such as a trajectory that includes one 360 degree coplanar arc, one 155 degree vertex arc, and two 180 degree arcs at couch angles 315 degrees and 45 degrees.

A rate at which the trajectory is followed may be fixed (e.g. a constant angular speed) or dynamically variable. Shaping of a radiation beam may be performed by a beam shaper, e.g. a MLC. In some cases, the beam shaper can be rotated or translated in addition to configured by positioning leaves or of the beam-shaping components.

Some non-limiting approaches generate a radiation treatment plan in a way that involves establishing a trajectory, defining control points on the trajectory, establishing beam shaping parameters for each of the control points and generating control signals for a radiotherapy system based on the collection of beam shaping parameters. The examples given in the following description employ approaches that use control points. However, the reader should bear in mind that control points are not fundamental to the concept of the invention as a whole.

Control points are typically assigned to points along a trajectory that are spaced reasonably closely. Radiation treatment parameter values (e.g. collimator configurations and/or radiation beam intensities) may be set for each control point. For points on the trajectory between adjacent control points some or all of the radiation treatment parameter values may be determined by interpolation between the corresponding radiation treatment parameter values for the adjacent control points. Specifying radiation parameter values for control points may be used to efficiently specify dynamic variation of radiation treatment parameters all along a trajectory.

In a simple example case where the trajectory is an arc, control points may be angularly spaced apart along the arc. Control points may be uniformly spaced apart, but this is not mandatory. In an example embodiment, adjacent control points are angularly spaced apart along an arcuate trajectory by angles of less than six degrees. For example, control points may be angularly spaced apart along the trajectory by angles of 2±1 degree or 2±½ degree. The following discussion of an example embodiment suggests control points every two degrees, but this is not mandatory.

In the present example, a configuration for a beam shaper (e.g. a MLC) is determined for each of the control points. The configuration may be based at least in part on the shapes and locations of the target volumes in a BEV corresponding to the control point. These shapes and locations may be determined from imaging of the patient (e.g. computed tomography (CT) and/or magnetic resonance imaging (MRI)), for example. The configuration for the beam shaper may be selected to define an aperture that follows boundaries of the projections of the target volumes closely.

In some embodiments, the beam shaper comprises a MLC and the beam shaper configuration comprises both positions of leaves of the MLC and an angle of rotation of the MLC.

Methods and apparatus may omit one or more target volumes in defining the aperture for one or more of the control points. Various methods may be applied to determine which target volumes will be omitted from consideration in establishing beam shaping parameters for which control points. When a target volume is omitted from consideration for a particular control point, the target volume can be said to be 'blinked' at that control point.

Blinking some target volumes at some control points can facilitate generation of a treatment plan that, when executed, will deliver the appropriate dose to each treatment volume. For example, lower-dose target volumes may be blinked at more control points than higher-dose target volumes. Appropriate selection of which control points to select for blinking a particular target volume may help to reduce dose to OARs. Appropriate selection of which control points to select for blinking a particular target volume may help to reduce dose to non-target tissues by allowing beam shaping better fitted to conform with the target volumes. Appropriate allocation of blinks among different target volumes may help to ensure that each target volume receives a corresponding prescribed dose.

To enable the efficient delivery of dose in some embodiments, the target volume(s) associated with the highest prescribed dose may be included in the definition of the aperture and the resulting beam shaping parameters for all control points.

In some embodiments one or more target volumes having prescribed doses lower than a maximum of the prescribed doses for all of the target volumes may be selected to be blinked. A proportion of the control points for which each target volume that has been selected for blinking will be blinked may be based on the prescribed dose of the selected target volume relative to the maximum prescribed dose.

In some embodiments, the proportion of the control points for which each target volume selected for blinking will not be blinked is set equal to or approximately equal to the quotient of the prescribed dose for the selected target volume and the maximum prescribed dose. For example where a maximum prescribed dose is 100 units, different particular target volumes may be blinked as shown in the following table:

| Prescribed dose for target volume | Control points to blink (%) | Control points not to blink (%) |
|---|---|---|
| 20 | 80 | 20 |
| 30 | 70 | 30 |
| 50 | 50 | 50 |
| 75 | 25 | 75 |
| 100 | 0 | 100 |

The highest-dose target volume may optionally be blinked for one or more control points. This may be desirable, for example, to reduce dose to an OAR and/or to allow for better beam shaping to other target volumes at selected control points. Where this is done the quota of control points for which other lower dose target volumes should be blinked may be set as a desired proportion of the quota of control points for which the highest-dose target volume is blinked. In some embodiments optimizations are performed to set quotas for blinking one or more target volumes.

Once it has been decided to blink a particular target volume for a number of control points, there are various ways in which the particular control points for which the target volume should be blinked may be assigned. The choice of control points to blink a target volume may be based on one or more factors, of which the following are non-limiting examples:

- whether the projection of the target volume overlaps with projections of one or more other target volumes in the BEV for certain control points;
- whether the projection of the target volume overlaps with, or is close to, projections of one or more OARs for certain control points;
- whether the configuration of target volumes is such that for the BEV of certain control points a beam shaper being used cannot be readily configured to conform to boundaries of the projections of the target volumes.

Figure 3:
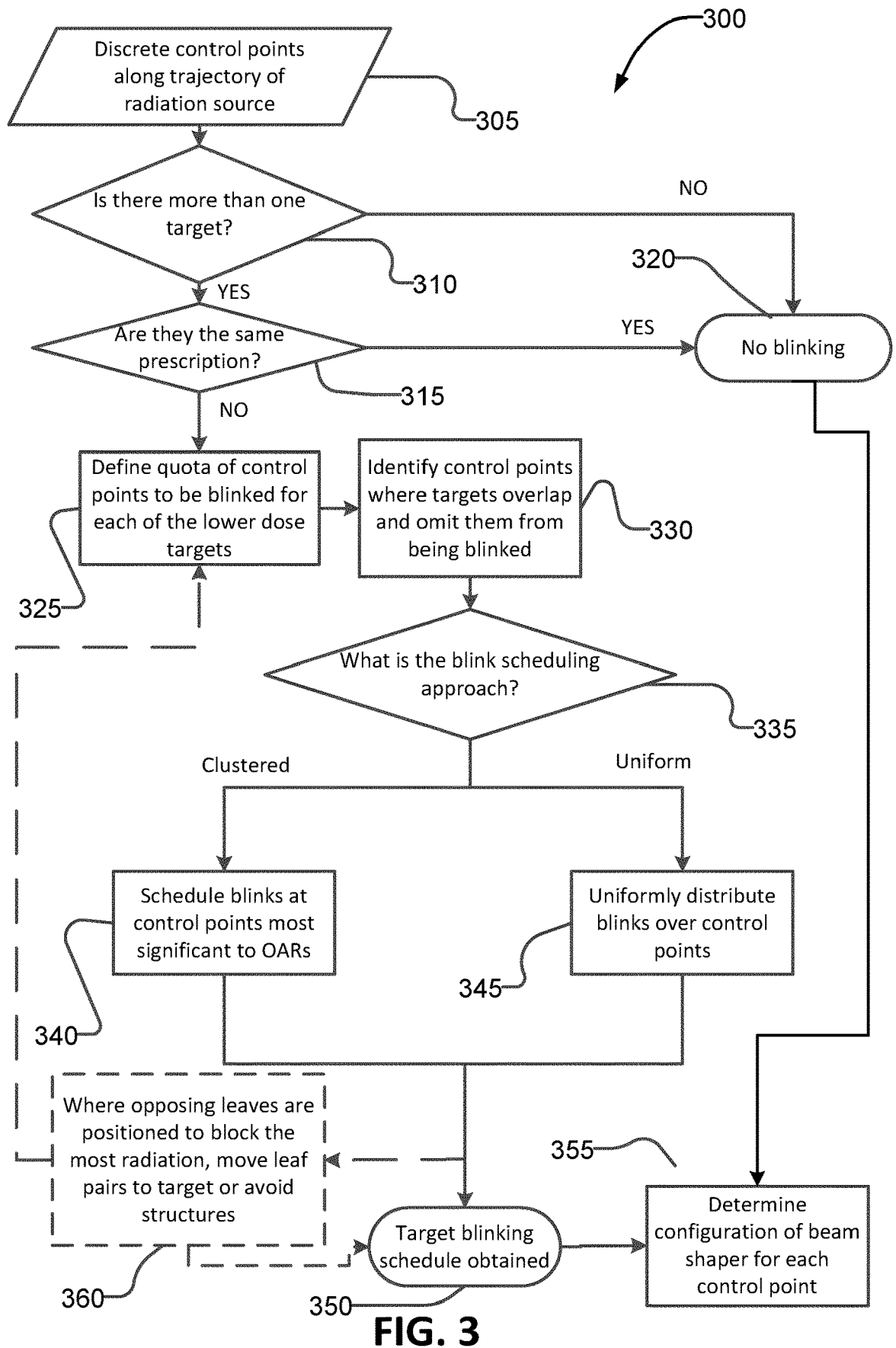
FIG. 3 is a flow chart for an example method for determining target volumes to be included or excluded from beam shaping calculations for a point on an arc therapy trajectory.

FIG. 3 shows a non-limiting example method 300 that may be performed to determine whether or not target volumes will be blinked at each control point along the treatment trajectory. At step 305, discrete control points along a trajectory of a radiation source are provided as input for method 300. The control points may be predetermined or provided in some other way. Step 310 determines whether there are two or more target volumes. If there is only a single target volume, method 300 continues to step 320 and no blinking is scheduled. Method 300 may optionally be modified to allow for blinking of the highest dose target volume whether or not there are other target volumes.

If there are plural target volumes at step 310, method 300 continues to step 315 which determines whether the multiple target volumes all have the same prescribed dose. If all of the target volumes have the same prescribed dose, method 300 continues to step 320 and no blinking is scheduled in this example. In other embodiments where the multiple target volumes all have the same prescribed dose some or all of the target volumes may be assigned a quota of blinks. For example, each of the target volumes may be assigned an equal quota of blinks.

In treatment scenarios where there are two or more target volumes with differing prescriptions, it may be beneficial for method 300 to calculate a quota of blinks for at least each of the lower dose target volumes in step 325. The quota may be a value indicating a number of control points for which the target volume should be blinked.

One metric that may be included in the calculation of the blink quota is the ratio of the lower dose target volume's prescribed dose to the prescribed dose assigned to the highest dose target volume. In a simple example, the quota may be set to the ratio of the lower dose target volume's prescribed dose to the prescribed dose assigned to the highest dose target volume multiplied by the total number of control points.

Relative output factor is another metric that may be included in the calculation of a blink quota for a target volume. The metric may compare a lower-dose target volume's average output factor to that of the highest-dose target volume. Output factors are widely used in radiation dosimetry and calibration of medical radiation sources. An output factor takes into account the fact that a target volume having a larger area in the BEV will tend to receive a larger dose than a target volume having a smaller area in the BEV because scattered radiation will contribute more to the dose in the target volume having the larger area.

The output factor may be determined for each target volume for each control point using calibration data which relates projected area in the BEV to output factor. Output factors for a target volume over all of the control points may then be summed or averaged. A ratio of total or average output factor for the lower dose target volume to that for a highest dose target volume may be used in a calculation to establish a quota of blinks for the lower-dose target volume.

For example, the following equation (1) may be applied to determine a blinking quota for any number of target volumes:

$$Q_{total,i} = CPT_{total} \cdot \left(1 - \left(\frac{Rx_i}{Rx_{max}}\right) \cdot \left(\frac{\overline{OF}_{max}}{\overline{OF}_i}\right)\right) \quad (1)$$

Where i is an index for target volumes in a treatment plan, $Q_{total,i}$ is the number of control points to be blinked for the $i^{th}$ target volume, $CPT_{total,i}$ is the total number of control points, $Rx_i$ is the prescribed dose for the $i^{th}$ target volume, $Rx_{max}$ is the highest prescribed dose for any target volume found in the treatment plan, $\overline{OF}_{max}$ is the mean output factor for the target volume with the highest prescription dose, and $\overline{OF}_i$ is the mean output factor for the $i^{th}$ target volume.

Other factors such as the average depths of different target volumes may be taken into account for establishing blink quotas for different target volumes. For example, target volumes that have greater average depths may be allocated quotas of fewer blinks, since radiation is attenuated as it travels through tissue. Target volumes having shallower average depths may tend to receive larger doses (everything else being equal). Such shallower target volumes may therefore be assigned quotas of more blinks.

In cases where the target volume having the highest prescribed dose is blinked at some control points the number of control points at which other target volumes are not blinked (e.g. as determined using Eqn. (1)) may be multiplied by the number of control points at which the highest dose target volume is not blinked divided by the total number of control points.

In some cases two or more target volumes may have the same prescribed dose (i.e. there may be a tie for the highest dose target volume). Such cases may be handled in any of various ways including:

- picking one of the highest dose target volumes to be the highest dose target volume, for example by random choice;
- using another characteristic of the target volumes as a tie breaker. The other characteristic may, for example comprise output factor, target volume average depth, or the like.

In step 330 method 300 identifies control points where projections of target volumes overlap in the BEV. It is generally undesirable to schedule a blink for one target volume at a control point where the projection of the target volume in question overlaps with the projection of another target volume (unless the other target volume will also be blinked at the same control point, which is an option in some embodiments).

Figure 4:
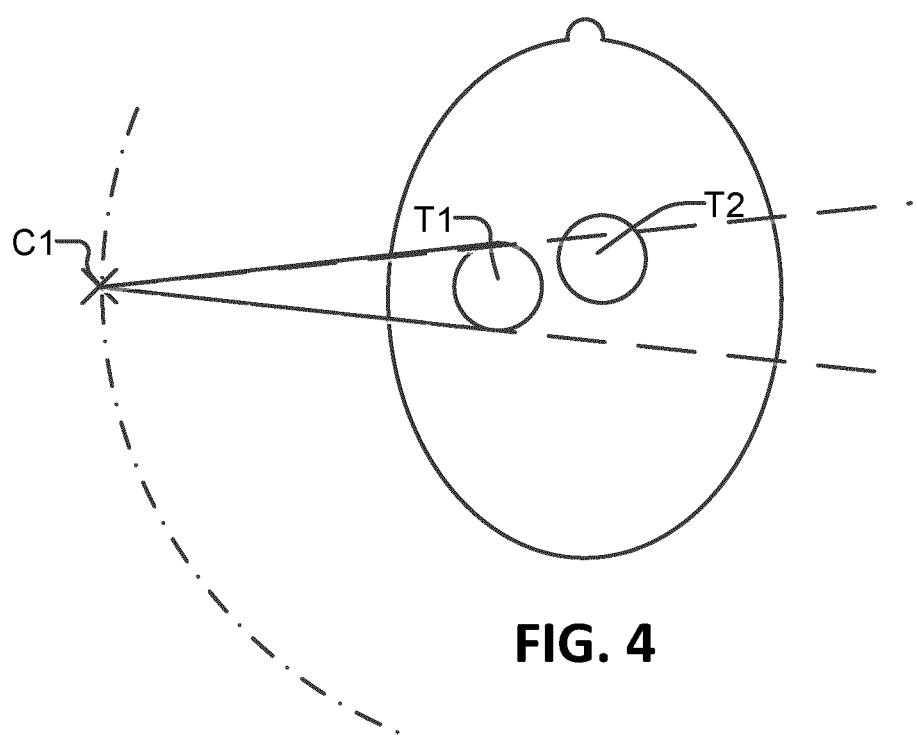
FIG. 4 is a schematic drawing showing two target volumes that overlap in the BEV for a particular beam direction.

For example, as illustrated by FIG. 4, it would not make sense to blink target volume T2 for the control point C1 because control point T2 will receive significant radiation dose from the radiation passing through target volume T1. For each target volume, step 330 may eliminate from consideration for blinking the target volume those control points in which the target volume overlaps with another target volume (with a possible exception where the other target volume can also be blinked).

Target blinking scheduling may then be performed to assign the quota of blinks for each target volume to specific control points. How this is done can affect the spatial distribution of blinks for a target volume along the treatment trajectory. Following step 330, the blink scheduling approach to be used for the treatment may be determined at step 335.

Different approaches to distributing the blinks may be employed. The approach may be selected by a user (e.g. a radiation oncologist or medical physicist responsible for establishing the treatment plan) in some embodiments. For example, a treatment planning system may implement plural algorithms for distributing blinks and a user interface that allows a user to select one of the algorithms to be applied. In other embodiments, a treatment planning system may apply plural algorithms for assigning blinks to control points in parallel and provide a user with metrics to allow results of the plural algorithms to be compared.

Some example algorithms for assigning blinks to control points may be designed to achieve the following objectives:
  try to spread blinks for each target volume out along the treatment trajectory as uniformly as possible;
  try to preferentially assign blinks to control points for which it is not practical to fit the beam shaper to conform well with boundaries of the projections of all of the target volumes (e.g. control points for which the best available configuration of the beam shaper allows a relatively large dose of radiation to be delivered to non-targeted tissues according to a suitable metric— one such suitable metric is whitespace as described below);
  try to schedule blinks for different lower-dose target volumes at different control points as often as possible;
  try to schedule blinks for each target volume at those control points that would otherwise contribute most to dose in one or more OARs;
  try to schedule blinks at each target volume at control points that would otherwise contribute most dose to non-target tissues;
  try to schedule blinks for a target volume for those control points for which there is the most overlying tissue between the target volume and the radiation source;
  try to avoid scheduling blinks in a way that would result in undesirably large or unachievable changes in beam shaper configuration between adjacent control points;
  combinations of two or more of these goals.

Any of these goals may be embodied in an algorithm for automatically scheduling blinks for one or more lower dose target volumes.

An algorithm for automatically scheduling blinks for one or more lower dose target volumes may, for example, compute a blinking goal metric for each control point that indicates a degree to which selecting that control point would satisfy a goal for distributing blinks. The control points may be ranked in order of the blinking goal metric. Blinks for each target volume may then be assigned to the control points until the quota of blinks for that target volume have all been assigned to control points. In some embodiments the algorithm marks some control points as being unavailable for blinking for one or more target volumes (for example because a target volume overlaps with another target volume in the BEV for that control point).

FIG. 3 shows an option 340 which permits clustering of blinks by placing more emphasis on avoiding dose to OARs and/or non-target tissues, and an option 345 which favours uniform distribution of blinks along the treatment trajectory. In some embodiments, a treatment planning system includes a user interface that permits a user to control aspects of the assignment of blinks to control points, for example, by one or more of:
  selecting one or more control points for which blinking is prohibited for one or more target volumes;
  assigning to one or more control points one or more penalty values which cause a blink assignment algorithm to favour or disfavor assigning blinks for one or more target volumes to the control point;
  manually assigning blinks for specific target volumes to specific control points;
  moving one or more control points on the trajectory (for example, to put a control point at a location on a trajectory where blinking can be more beneficial, for example for sparing dose to an OAR);
  etc.

Method 300 yields target blinking schedule 350.

FIG. 6A shows an example of a possible result of option 340 in method 300 where 'clustering' is the selected blinking approach. FIG. 6A shows the control points B where a lower dose target volume T3 is not targeted. Control points for blinks are selected to avoid delivering dose to OAR 400, with the result that the blinks are spatially clustered. Target volume T3 is not targeted at control points with a high degree of overlap with OAR 400. Disadvantages of clustering blinks include: there may be a bias in the spatial distribution of dose to targets. This could result in streaks of elevated dose to non-target tissues.

FIG. 6B shows an example of option 345 in method 300 where uniform distribution is the selected blinking approach. FIG. 6B shows the control points B where a lower dose target volume is not targeted. In this example, blinks are distributed approximately uniformly along a trajectory. Uniform distribution of blinks can mitigate the bias in spatial distribution by ensuring the delivery of dose to target volumes over a wide range of beam angles. However, uniformly distributing blinks may not allow the treatment plan to minimize dose to OARs as well as cases which permit more spatial clustering of the blinks.

Figure 5A:
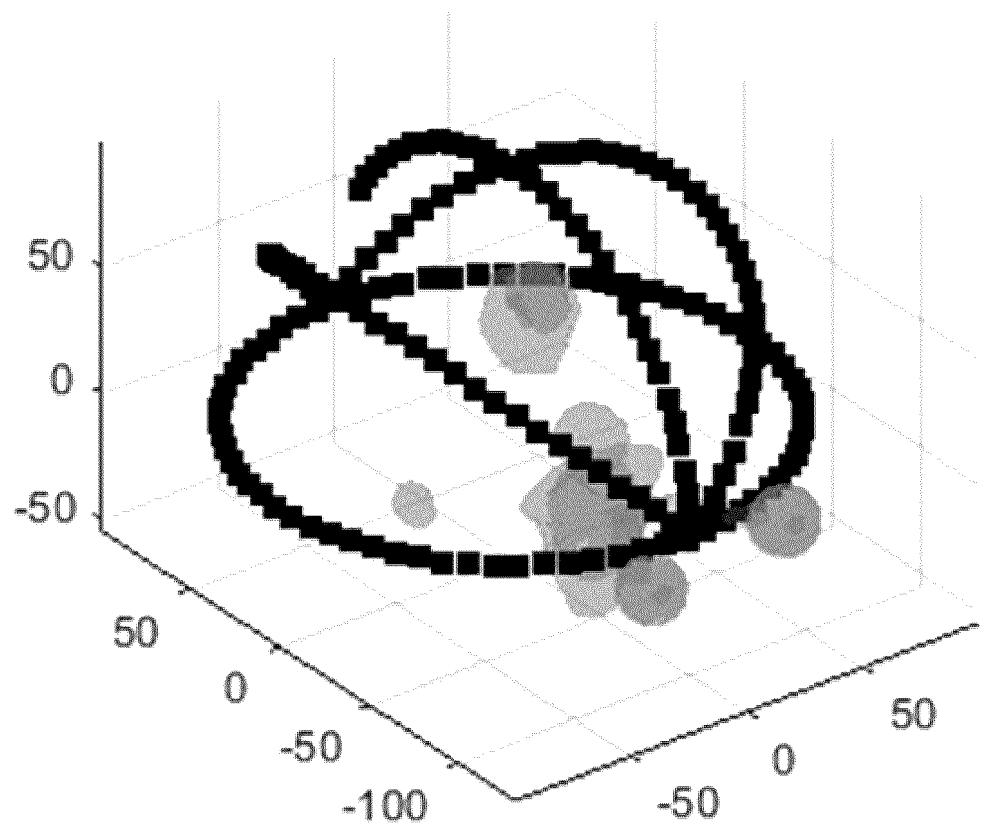
Figure 5B:
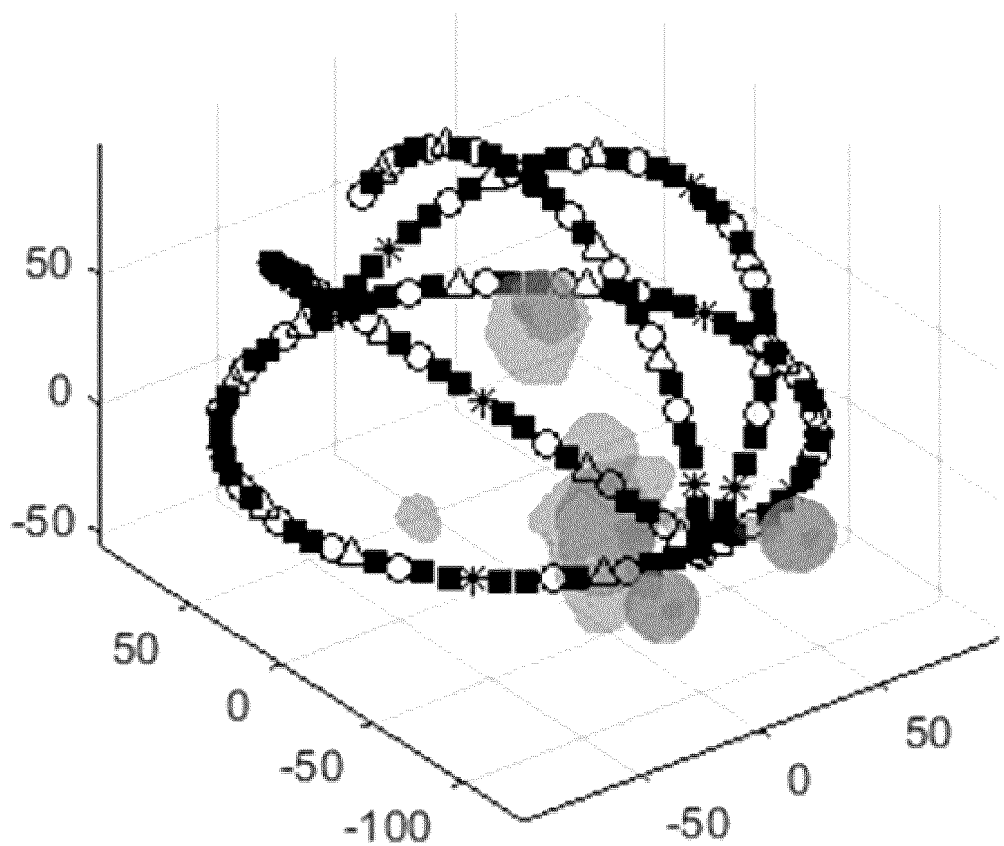
Figure 5C:
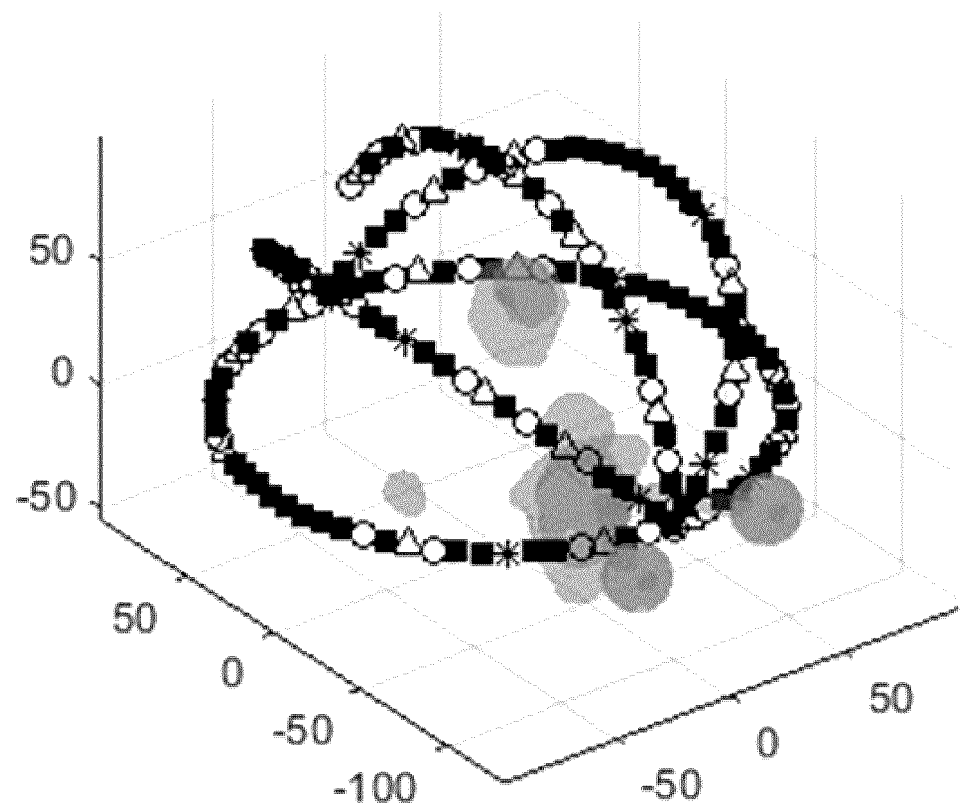
Figure 5D:
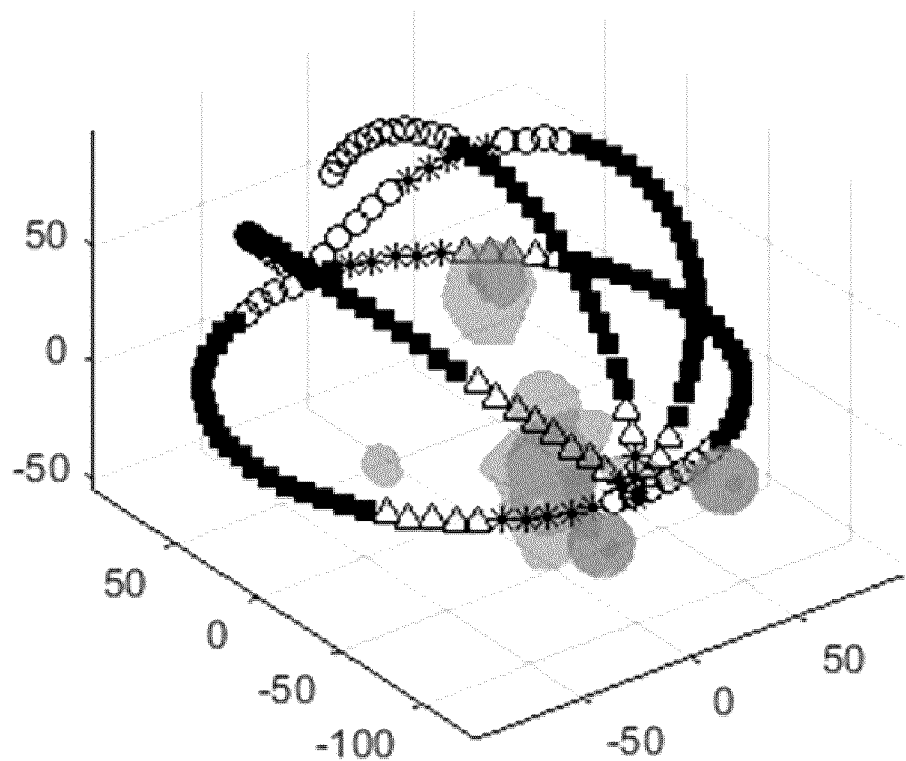
Figure 5E:
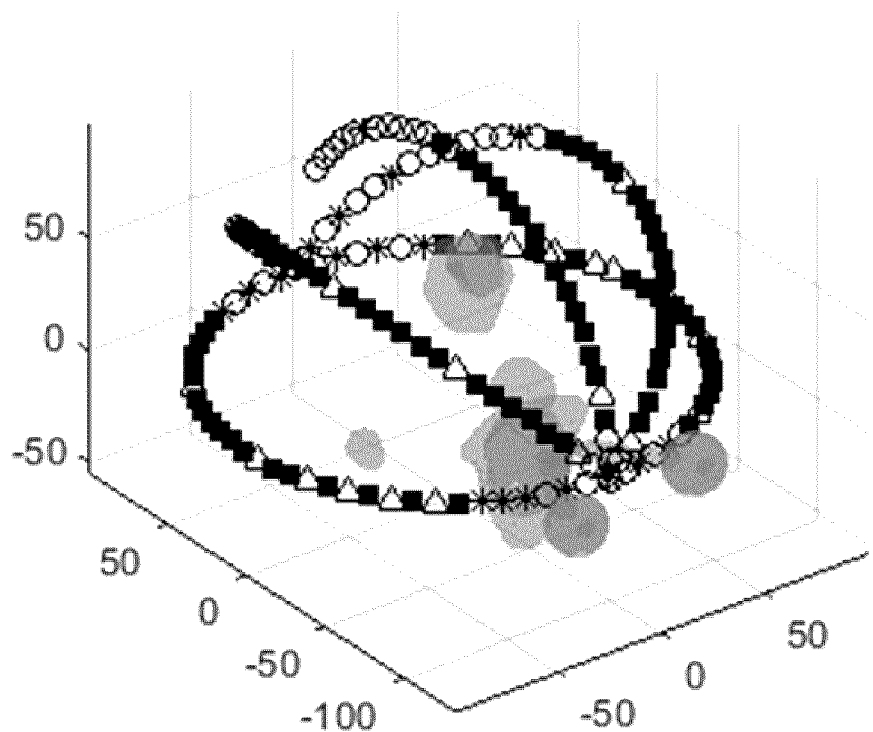
Figure 5F:
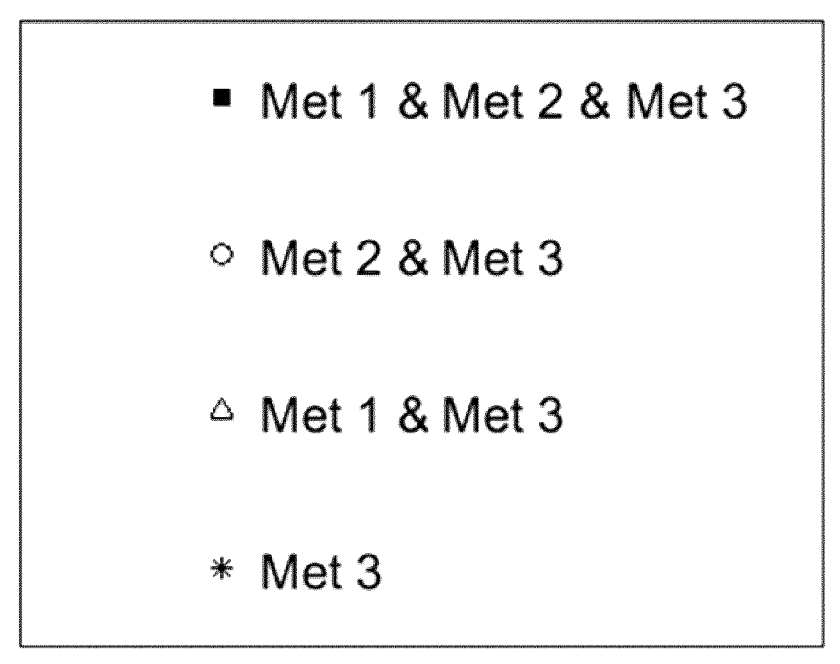

FIGS. 5A to 5E show example outputs for different possible blink assignment approaches which have yielded different blinking schedules. FIG. 5F is a legend representing the targets being treated at each control point, with 'Target 3' in the example being the maximum-prescription-dose target. FIG. 5A shows an example where blinking is not performed. The aperture for each control point is open for each target volume. FIG. 4B shows an example where blinks are distributed uniformly across the treatment trajectory. FIGS. 5C-5E illustrate examples where targets that overlap at a control point will not be blinked. FIG. 5C shows an example where blinks are uniformly distributed to all remaining available control points. FIG. 5D shows an example where blinks are allowed to cluster at control points where the target volume overlaps with one or more OARs in the BEV. FIG. 5E shows an example where blinks are first uniformly distributed across control points for which the target volume overlaps with an OAR by more than a threshold amount and the remaining blinks (if any) are distributed uniformly across the treatment trajectory.

Methods as described herein may be applied to any arc therapy treatment trajectory. Treatment plans may involve any suitable number of arcs. A wide range of alternative algorithms that may be used for determining arc therapy treatment trajectories are described in the technical literature and/or embodied in commercially available systems.

The inventors consider that there can be beneficial synergies when the methods described above are applied in contexts where a treatment trajectory specifies motions of both the patient and a radiation source. Some embodiments provide control signals to drive motions of a patient support, such as patient support couch 140 shown in FIG. 1. Some embodiments comprise patient supports that are movable under control of a radiation treatment machine in multiple degrees of freedom. Such movable patient supports are commercially available.

Target blinking methods as described herein may be used optionally and beneficially in combination with systems and methods which identify optimal delivery angles and provide additional degrees of freedom. 4π Optimization is a method for optimizing treatment trajectories involving both gantry and patient support couch motion for use in radiotherapy. 4π Optimization is described, for example in PCT international application publication No. WO2016008052A1 which is hereby incorporated herein by reference for all purposes.

PCT international patent application publication No. WO2016008052A1 discloses quantifying the degree of geometric overlap between planning target volumes and OARs and their relative depths relative to the radiation source in order to obtain an objective function (4π objective function). A suitability map may then be generated for every valid combination of couch and gantry angles using the 4π objective function to find an optimal trajectory. The use of this optimization technique and the generation of a suitability map provides strong synergies with the present invention by providing an optimized trajectory and set of control points. Additionally, the 4π objective function may be used beneficially in the context of the present invention to identify the control points, if any at which specific target volumes have at least some degree of overlap with an OAR. This information may be applied to assist determination of the control points at which a specific lower-dose target volume will be blinked.

Target volume blinking may be used beneficially with systems which shape the radiation beam to conform to target volumes. After obtaining a target blinking schedule in step 350, method 300 may continue to step 355 to determine the configuration of the beam shaper for each control point. A projection of each of the specified target volumes in the beam's-eye-view (not including any target volumes being blinked for the control point) can be used to determine a configuration of a beam shaper to provide an aperture that better fits to the perimeters of the target volumes.

In some embodiments of the systems and methods which determine the optimal beam shapes for each control point, a measure relating to radiation dose delivered to non-targeted tissues is used in a metric to find optimal beam shapes subject to constraints such as the ability of a particular beam shaper to match certain profiles and limitations on how quickly the configuration of the beam shaper can be changed. One suitable measure that may be used may be called a "whitespace measure".

Example systems and methods which apply a whitespace measure to optimize a set of beam shapes for control points over a trajectory is disclosed in PCT International Application No. PCT/CA2017/050315, published as WO 2017/152286 A1 which is hereby incorporated herein by reference for all purposes. The inventors consider that significant synergies may be achieved by using the blinking techniques described in the present application with optimization of beam shaping parameters as described in PCT/CA2017/050315.

There may be configurations of plural target volumes for which a particular beam shaper such as a MLC cannot effectively block radiation to non-target tissues while delivering dose to the target volumes. FIGS. 7A and 7B illustrate an example of this. FIG. 7A shows target volumes T5, T6 and T7 in the BEV of a particular control point. MLC 200 is set to provide an aperture to deliver radiation to all of the target volumes (T5, T6 and T7), resulting in substantial whitespace between targets T6 and T7 due to the mechanical restrictions of the multi-leaf collimator. Attempting to remedy this situation by rotating MLC 200 would result in poor beam shaping along the concave part of target volume T5. It is not possible for leaves 222 of MLC 200 to provide an aperture that exposes all of target volumes T5, T6 and T7 without also targeting a large area of non-targeted tissue.

Omitting one or more lower dose targets at certain control points through target blinking may help to reduce dose to non-targeted tissue because the MLC or other beam shaper may be configured to provide an aperture that better fits to perimeters of the remaining target volumes. FIG. 7B illustrates that through target blinking, and omitting the treatment of certain lower dose targets at a control point, a whitespace measure may be improved. After target volume T7 is blinked and blocked by the leaves of MLC 200, MLC 200 is able to achieve a better fit around target volumes T5 and T6 and is able to avoid leaving whitespace between target volumes T6 and T7 as encountered in FIG. 7A.

Figures 7C, 7D:
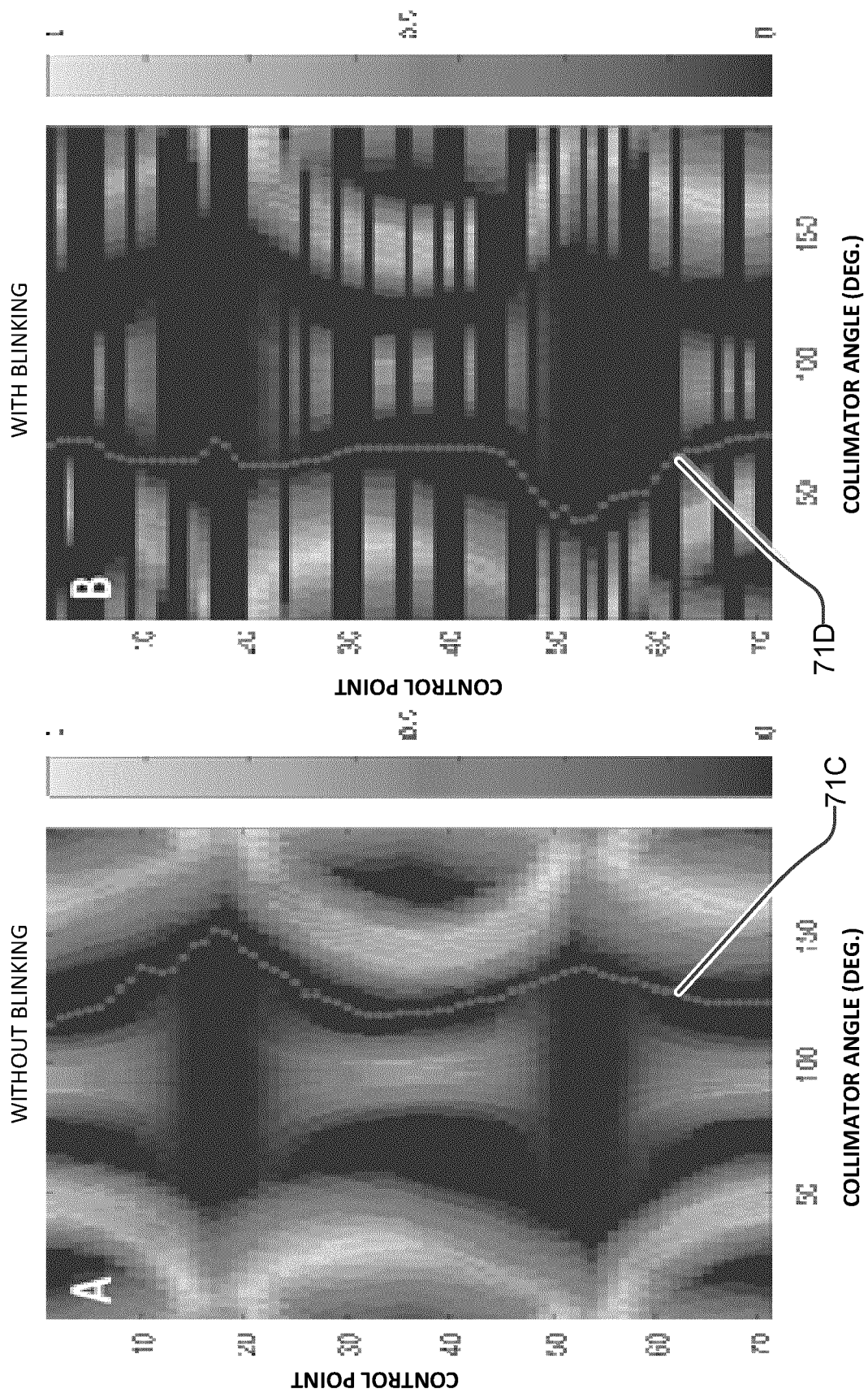
FIGS. 7C and 7D are whitespace maps for a group of target volumes respectively without and with blinking as described herein.

Selectively not treating certain target volumes for some beam directions can result in collimator trajectories that can significantly reduce dose to non-target tissues. FIG. 7C shows an example whitespace map in which all target volumes are treated for all beam angles. In FIG. 7C darker areas correspond to less whitespace (less dose to non-target tissues) and lighter areas correspond to more whitespace (more dose to non-target tissues). FIG. 7C shows an optimized trajectory 71C. By contrast, FIG. 7D is a whitespace map for the same target volumes as FIG. 7C with the difference that the principles of the present disclosure are applied so that not all target volumes are treated for all beam angles. FIG. 7C shows an optimized trajectory 71D. Comparison of FIGS. 7C and 7D shows immediately that the whitespace maps are significantly different with the result that optimized trajectory 71C is very different from optimized trajectory 71D. Improved optimized trajectory 71D provides a reduced whitespace measure which is made possible by fitting an aperture for each beam direction only to targets that are selected for treatment for that beam direction Instead of fitting the aperture to all targets for every beam direction.

A target volume blinking schedule may be used optionally and beneficially in combination with a MLC which can be rotated during delivery of radiation about the beam axis. Such an embodiment allows for an algorithm to further optimize the trajectory of the MLC's leaf configuration and rotation angle to better match the contours of targets to optimize the whitespace measure.

The foregoing description has not discussed the intensity of radiation to be delivered at points along a treatment trajectory. In some embodiments, the intensity of radiation is maintained constant along the treatment trajectory. In other embodiments, the intensity of radiation may be varied along the trajectory.

A monitor unit (MU) in radiotherapy is a measure of output from a radiation source (e.g. a linear accelerator). Monitor units are measured in order to ensure an accurate dose according to the treatment plan.

Some embodiments of the present invention provide systems and methods for improving treatment plans by optimizing monitor unit distribution. The methods described herein provide a structure for optimizing distribution of monitor units along a trajectory. This structure may be used beneficially in combination with target volume blinking. The disclosed structure for monitor unit distribution may also be implemented independently of target volume blinking in any system configured to provide arc therapy treatment planning.

Figure 8:
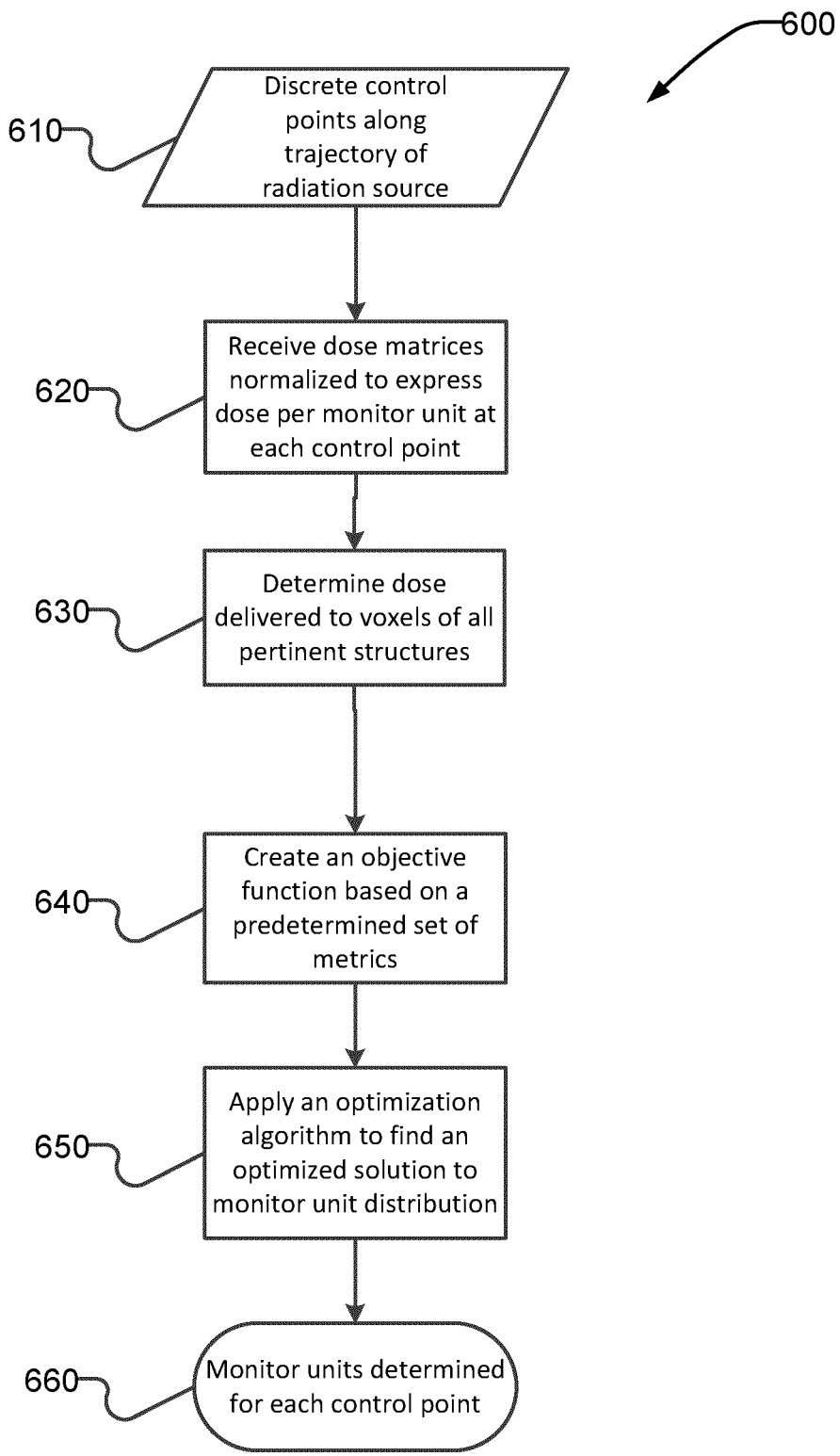
FIG. 8 is a flow chart for an example method for optimizing monitor unit distribution.

FIG. 8 is a flow chart showing an example method 600 that may be performed to optimize monitor unit distribution in a treatment plan. At step 610, discrete control points along a trajectory of a radiation source are provided. Step 620 receives dose matrices from radiation treatment planning software. These dose matrices may be normalized to express dose per monitor unit at each control point. Step 630 uses the dose matrices to create a data structure containing dose information to voxels of all pertinent structures (e.g. target volumes, OARs and/or non-targeted tissues outside of OARs). Using an objective function provided in step 640 and the data structure of step 630, an optimization algorithm is executed in step 650 to yield an optimized solution to the distribution of monitor units for each control point at step 660.

Because a distribution of dose where one or more control points is scheduled to receive radiation can be rescaled to achieve prescribed doses to individual target volumes, there are an infinite number of solutions to distributing monitor units among control points. Therefore, the quantity of data to manage and analyze in the optimization of monitor unit distribution during arc therapy can be enormous.

Step 620 of method 600 may involve using radiation treatment planning software to export a 3-dimensional matrix of dose information for each control point. These matrices contain information about how dose is delivered at each control point and also contain data pertaining to the three-dimensional pixels (or voxels) located within the structure boundary of all pertinent structures (e.g. targets, OARs).

The normalized dose matrices may be filtered to identify the voxels within the structures' boundaries in step 630. The dose applied to the voxels within these structures may be determined and then be divided by the amount of monitor units scheduled to be delivered at the control point according to the dose matrix. These voxel values may then be indexed according to the structure and control point information. This creates a data structure in which all dose information for a given control point and a given structure can be easily accessed. Furthermore, this structure allows for rescaling and combining potential monitor unit distributions without the need to manipulate entire dose matrices.

An objective function may be initialized to optimize several dosimetric quality metrics in step 640. Such metrics may include target coverage, target dose homogeneity, normal tissue sparing, and maximum OAR dose. By quantifying the quality of every relevant metric, an optimal solution of monitor unit distribution may be determined by minimizing the objective function. The total objective function used to define the quality of a candidate monitor unit distribution may be defined as the sum of all metrics defined for all structures in that distribution.

A penalty function may optionally be included in the objective function in step 640. The penalty function may facilitate balancing of two or more dosimetric quality metrics by accounting for the degree to which a candidate distribution does not meet one or more of the desired values of the quality metrics.

In some embodiments, for one or more metrics a system as described herein may configure a 'must' value, a 'warn' value, and a 'penalty' value corresponding to the 'warn' value. A linear-quadratic metric penalty function may then be created to translate the value of a given metric into a penalty score according to these assigned values.

Figure 9:
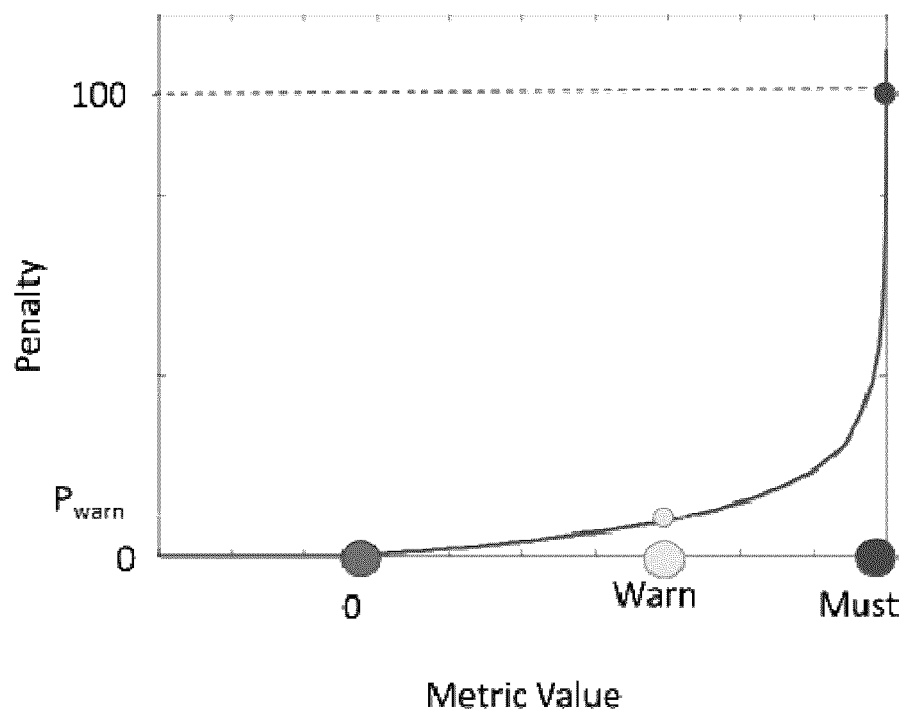
FIG. 9 is a graph illustrating an example penalty function.

FIG. 9 shows an example linear-quadratic penalty function for which a penalty score on the y-axis is a function of the value of a corresponding metric on the x-axis. The penalty function may be defined by a linear function defined by the points [0,0] and [warn, $P_{warn}$] and a concave-up quadratic function thereafter defined by the points [warn, $P_{warn}$] and [must, 100].

An optimization algorithm may apply the resulting objective function to establish an optimal monitor unit distribution. The optimization algorithm may use the data structure produced in step 630 for increased efficiency.

In some embodiments, the optimization algorithm applied in step 650 is a simulated annealing algorithm. Techniques for simulated annealing are well known in the art. For example, simulated annealing techniques are disclosed in Optimization by Simulated Annealing, S. Kirkpatrick et al., 1983, and Science and Thermodynamical approach to the travelling salesman problem: An efficient simulation algorithm, V. J. Cerny, 1985, *Journal of Optimization Theory and Applications*. As input, the simulated annealing algorithm may take an initial solution (which may be randomly generated) and the associated objective function value. The algorithm may then select a random control point and for the selected control point a random amount (within an allowable range) to vary the monitor units associated with the selected control point. If the change improves the objective function score, it is accepted as the new distribution. If the change worsens the score, there is a probability of accepting the worsened distribution in the search for a global minimum.

For example, the following equation may be employed for the determination of the probability a worsened score is accepted.

$$P = e^{\frac{OF_{old} - OF_{new}}{T}} \quad (2)$$

Where P is the probability of accepting the change to the distribution, $OF_{new}$ is the objective function value after the change, $OF_{old}$ is the objective function value before the perturbation, and T is the 'temperature' at the current iteration. At each iteration, the temperature is decreased by a multiplicative constant denoted as the cooling rate. As such, the probability of accepting a worsened distribution is decreased as the simulated annealing progresses.

Figure 10A:
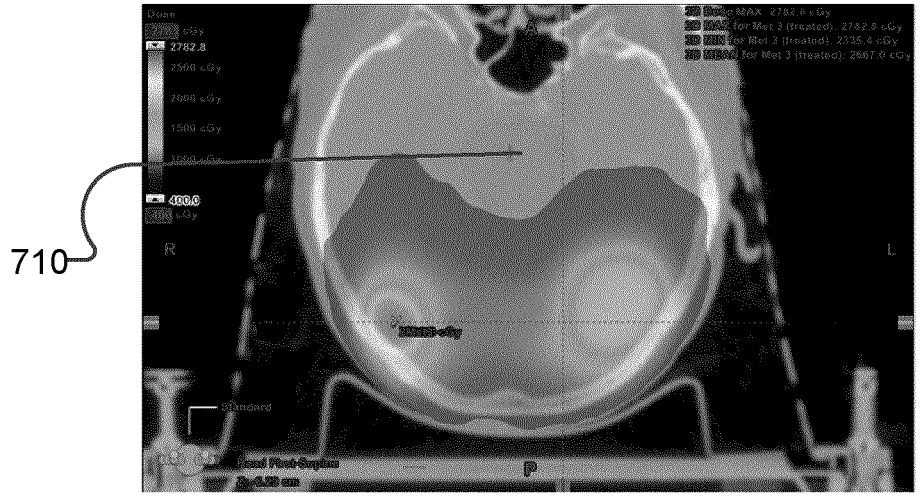
FIGS. 10A and 10B show example dose distributions for an optimized treatment and a non-optimized treatment, respectively.
Figure 10B:
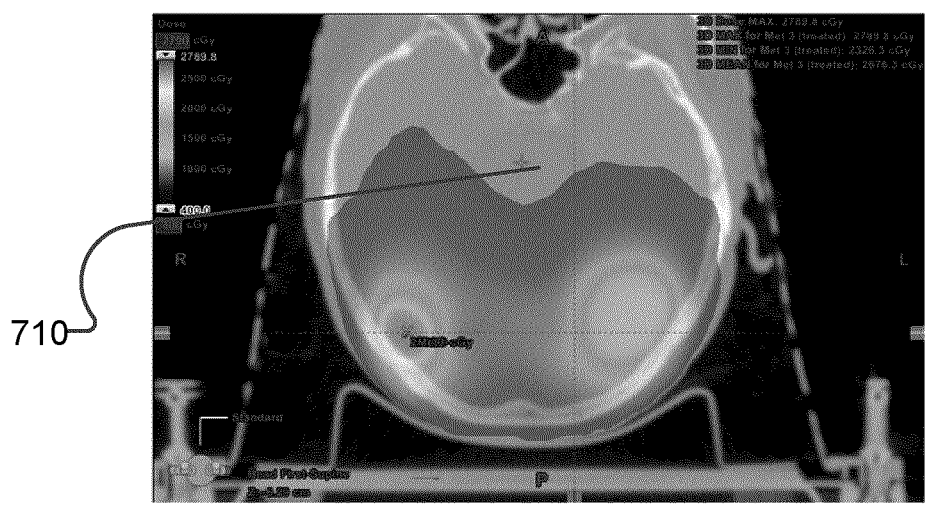

The use of an optimization algorithm in determining distribution of monitor units among control points increases the probability of locating a global solution where the total objective function is minimized. A comparison of FIGS. 10A and 10B illustrates how an improved monitor unit distribution can result from the use of an optimization method as described herein. FIG. 10A shows a monitor unit distribution selected using a simulated annealing optimization algorithm with 10,000 permutations. This approach found a solution in which significant radiation dose to OAR 710 is almost entirely avoided. FIG. 10B shows for comparison a monitor unit distribution selected through 100,000 random attempts which applies a significantly higher dosage of radiation to OAR 710.

In an example embodiment a simulation is prepared and initialized for use in simulated annealing. For example, the simulation may be initialized with all targets being treated at all control points. The same contribution of monitor units may be specified for every control point. Parameters (e.g. for how many control points is each target volume blinked, how many monitor units are delivered at each control point, for which control points is a particular target volume blinked) may then be varied according to a simulated annealing algorithm. The overall quality of each set of parameters may be assessed using a suitable objective function.

In some embodiments an objective function employed for both blinking (schedule and quota) and control-point specific monitor unit distribution is given by the following equations, where M is the penalty at metric value v, k is the number of metrics applied to the $i^{th}$ PTV, p is the number of targets, and o is the number of OARs:

$$M = \begin{cases} \frac{p_{warn}}{v_{warn}} v, & \text{if } 0 < v < v_{warn} \\ \frac{100 - p_{warn}}{v_{must} - v_{warn}} [v - v_{warn}]^2 + p_{warn}, & \text{if } v \geq v_{warn} \end{cases} \quad (A)$$

$$OF_{PTVj} = \sqrt{\sum_{i=1}^{k} M_i^2} \quad (B)$$

$$OF_{PTV} = \sum_{j=1}^{p} OF_{PTVj} \quad (C)$$

$$OF_{OAR} = \sum_{i=1}^{o} M_i \quad (D)$$

$$OF_{PLAN} = OF_{PTV} + OF_{OAR} \quad (E)$$

This is an example of an objective function in which objective function components for individual target volumes are combined and objective function components for individual OARs are combined and the resulting combinations are combined to yield an overall objective function for a plan. Specifically, in this example case:

The OF for an individual target (OFPTVi) is a quadrature addition of the target metrics (Mi).
The total OF for all targets (OFPTV) is a linear sum of the OFPTVi.
The total normal tissue OF (OFOAR) is a linear sum of normal tissue metrics, one for each OAR.
The plan quality objective function (OFPLAN) is the sum of target and normal tissue objective functions.

Different objective functions that may be used in other embodiments may be obtained by modifying one or more of Equations (A) to (E) to use different ways to combine the individual components in Equations (A) to (E). For example, combinations of different OF components may be made by: linear summing, weighted summing, quadrature summing, averaging etc.

In this example the OF is calculated from metrics (M) based on a linear-quadratic penalty function. Such a penalty function may be more appropriate for typical SRS planning constraints that are often focused primarily on maximum doses to normal tissues or minimum coverage of a target. The value of M was defined arbitrarily to be 100 at the value of the clinical constraint (or limit of acceptability), denoted here as $v_{must}$. A $v_{warn}$ value was also employed. The value of M increases more rapidly if $v_{warn}$ is exceeded. The value of M is non-zero for OARs for any non-zero dose. For targets, M takes on a non-zero value for any deviation from a perfect DVH (i.e. unless all target voxels receive exactly the prescription dose). The particular value of M in Equation (A) is calculated with a quadratic which intersects the points [vmust, 100] and [$v_{warn}$, $p_{warn}$], where $p_{warn}$ is the value of M at the value $v_{warn}$, and a linear function from [0,0] to [$v_{warn}$, $p_{warn}$].

In some embodiments, in order to ensure that the simulation does not produce a result with a very high percentage of the control points closed throughout the treatment plan (which might undesirably reduce the efficiency of the plan or bias the intermediate level dose distribution to meet the prescription doses from very few similar incident directions, a penalty function may be applied to the total number of blinks for a given target. The penalty function may, for example, be a linear-quadratic penalty function.

In some embodiments a penalty function, $v_{must}$ is given by the total number of control points, and $v_{warn}$ is a predetermined fraction (for example a fraction in the range of 35% to 70% or a fraction that is approximately 50% of the total number of control points). The penalty may be included in equation (E). For example, the penalty may be added to equation (E) to yield the following equation that includes the penalty:

$$OF_{PLAN} = OF_{PTV} + OF_{OAR} + OF_{NOB} \quad (F)$$

Where $OF_{NOB}$ is the objective function which includes or consists of the penalty for the total number of blinks (NOB).

Figure 11:
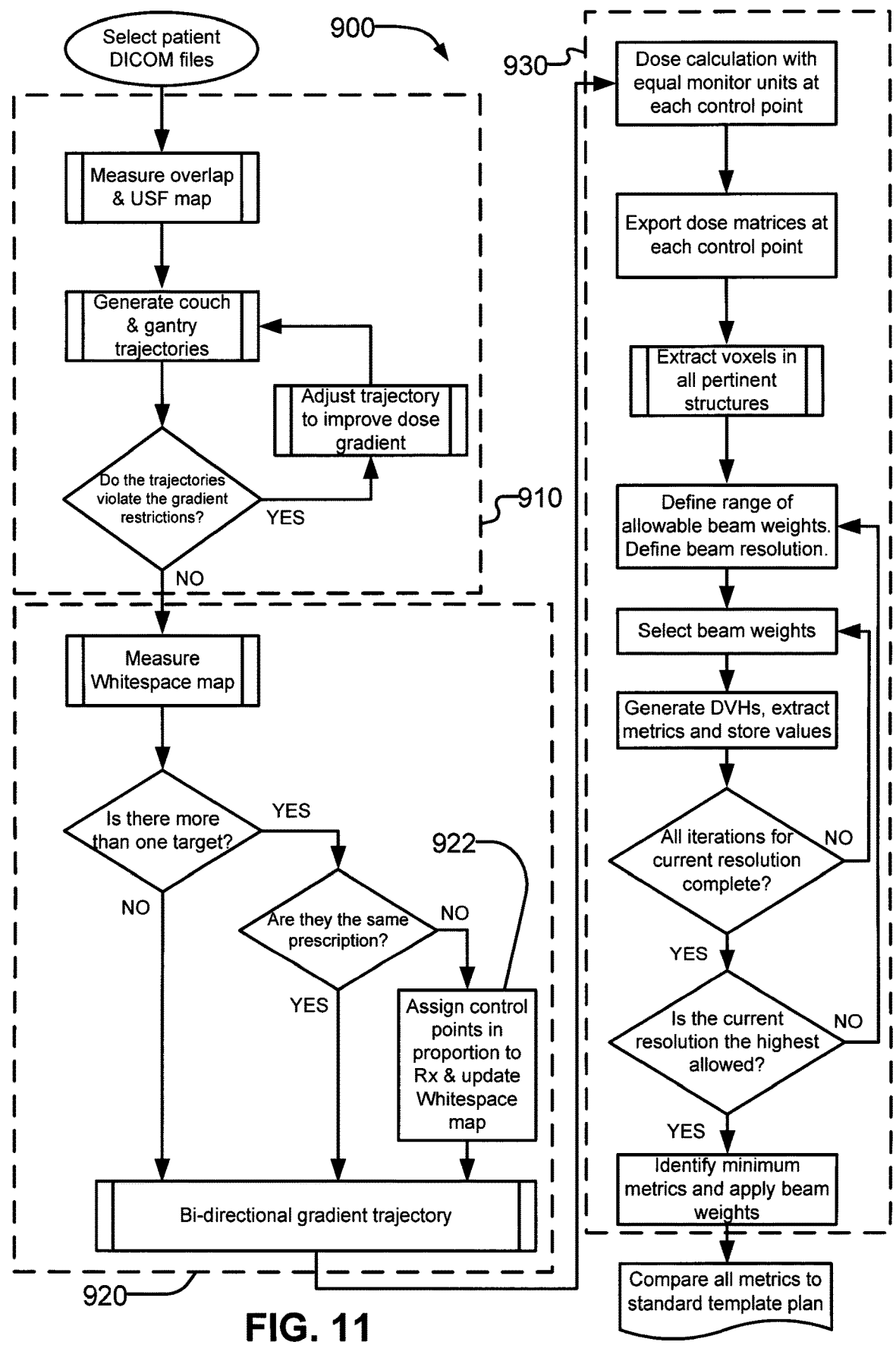
FIG. 11 is a flow chart of a radiation treatment planning method according to an example embodiment.

FIG. 11 illustrates an example method 900 according to a more specific embodiment of the invention. Method 900 incorporates trajectory planning 910, collimator trajectory planning 920 which includes a blinking step 922, and monitor unit distribution planning 930. In some embodiments, trajectory planning 910 applies methods and/or apparatus as described in WO2016008052A1. In some embodiments, collimator trajectory planning 920 applies methods and/or apparatus as described in PCT International Application No. PCT/CA2017/050315.

MLC configurations will often include cases for which opposing MLC leaves 222 abut end-to end (i.e. cases where for a particular control point the paths of the abutting MLC leaves 222 do not cross the BEV projections of any target volumes). The line along which the ends of opposing MLC leaves abut is usually a source of radiation leakage. This leakage may be called "abutting leaf leakage" or "ALL"

Some embodiments of the present invention control the locations at which pairs of opposing MLC leaves abut to optimize a distribution of dose. Such control may optionally be performed independently of features of other embodiments described herein as a separate method or by apparatus configured to provide such control. Such control may also be performed in combination with any features of any of the embodiments described in this disclosure or any combination of such features. For example, the abutment location may be positioned to add dose to a location in a blinked target volume that would otherwise receive less than the dose prescribed for that target volume. Positioning of leaf abutment locations may also be optimized to reduce or avoid excess dose to any tissues within a patient.

In some embodiments, a treatment plan is established as discussed herein. After the treatment plan has been established the total dose that would be delivered to voxels in a patient by a radiation source operating to deliver the planned radiation may be calculated. The calculation may be based, for example, on a model which takes into account the interactions of radiation with the tissues of the patient. For example, the model may take into account factors such as radiation scattering, radiation absorption, the nature of the radiation, and/or the distribution of different tissue types within the patient. Such models are known and understood by those of skilled in the art.

Voxels that will receive dose via ALL for different leaf abutment locations may be determined, for example by ray tracing. Positions for the leaf abutment locations may be selected to achieve one or more of:
improved dose uniformity in one or more target volumes;
reduced dose to one or more OARs;
reduced dose to non-target tissues;
etc.

In an example embodiment, the model does not take into account ALL. In such embodiments, the contribution to dose from ALL may be determined separately and used for optimization as above.

In some embodiments, leaf abutting positions are caused to dynamically vary between control points by picking first and second different leaf abutment positions for adjacent control points, thereby causing the leaf abutting position to sweep between the first and second positions, thereby spreading the dose due to ALL over an area.

In an example embodiment, a method for optimizing leaf abutting positions comprises generating a histogram that indicates the frequency over a treatment plan over which each voxel within each target volume receives dose due to ALL. If certain voxels of a target volume are disproportionately affected by ALL (high frequency in the histogram), the leaf abutting positions may be perturbed to redistribute the ALL within the target volume.

In some embodiments, the optimization of abutting leaf positions is performed only for leaf positions that abut because of blinking of one or more target volumes as described herein. In other embodiments, the optimization of abutting leaf positions is performed for some or all abutting collimator leaves in a treatment plan, whether or not those abutting leaf positions result from blinking a target volume.

In some embodiments, a calculated dose distribution is processed to locate parts of treatment volumes where the dose is calculated to be below a prescribed dose. Abutting leaf positions may then be selected to "top up" the dose in such underdosed parts.

Allocation of leaf abutment locations may be performed as part of an iterative process that includes setting quotas of blinks for different target volumes. This is indicated schematically by optional block 360 in FIG. 3. For example, a particular calculated dose distribution may result from a set of quotas for blinks for different target volumes and a particular allocation of those blinks across control points. The additional dose from ALL may then be quantified and allocated by determining abutting leaf positions. Analysis of the total resulting dose may suggest that the blink quota for one or more target volumes should be increased or decreased. For example, it may be desirable to increase the blink quota (more blinks) for a target volume for which the total dose, including the dose from ALL, exceeds a prescribed dose. As another example it may be desirable to decrease the blink quota for a target volume for which the total dose, including the dose from ALL is less than a prescribed dose. Another iteration may then be performed using the updated blink quota. This process may be continued for a desired number of iterations and/or until a termination condition has been satisfied.

Some example embodiments provide the following workflow:
1. Measure 4π objective function score map for every individual target volume (PTV) against all OARs in consideration.
2. Measure 4π objective function score map for every unique pair of PTVs.
3. Measure Whitespace objective function score map for every PTV individually, and every unique combination of PTVs.
4. Generate couch-gantry trajectory (CGT) via DCGT algorithm from 4π objective function map for all PTVs combined.
5. Measure objective function value of CGT on:
   a. 4π objective function score map from every individual PTV.
   b. Output factor of every individual PTV.
6. Define quota of control points assigned to shield each target volume based on prescription ratio and mean output factor ratio.
7. Determine control points in which to shield low-prescription targets based on ensuring all control points with overlap between two or more PTVs are open, and uniformly distribute the blinking quota over all non-zero PTV/OAR overlap control points (FIG. 5*e*).
8. Create composite whitespace objective function score map from cropped maps corresponding to proper number of targets (measured in point 3 above) at each control point from point 7 above. Apply blurring filter to map to ensure sharp discontinuities are removed.
9. Generate collimator-control point trajectory (CCPT) via bi-directional gradient algorithm from composite whitespace objective function score map generated in point 8 above.
10. Calculate dose without modulation, and optimize the monitor unit distribution via simulated annealing using a linear-quadratic penalty guided objective function.

Another example workflow operates as follows:
1. Measure 4π objective function score map for every individual PTV against all OARs in consideration.
2. Measure 4π objective function score map for every unique pair of PTVs.
3. Measure Whitespace objective function score map for every PTV individually, and every unique combination of PTVs.
4. Generate binary mask from 4π objective function score map for all PTVs combined with all values below threshold value of n % of the maximum value in map set to 0 and all values above threshold set to 1.
5. Generate trajectories in the binary mask which use only coordinates with values equal to 0, and comply with a user defined mechanical travel restriction, from random sampling.
6. For every trajectory generated in point 5:
   a. Measure objective function value of CGT on:
      i. 4π objective function score map from every individual PTV.
      ii. Output factor of every individual PTV.
   b. Define quota of control points assigned to shield each target volume based on prescription ratio and mean output factor ratios.
   c. Determine control points in which to shield low-prescription targets based on ensuring all control points with overlap between two PTVs are open, and uniformly distribute the blinking quota over all non-zero PTV/OAR overlap control points (FIG. 5E).

d. Create composite whitespace objective function score map from cropped maps corresponding to proper number of targets (measured in 3) at each control point from c. Apply blurring filter to map to ensure sharp discontinuities are removed.
e. Generate collimator-control point trajectory (CCPT) via bi-directional gradient algorithm from composite whitespace objective function score map generated in point 6d.
f. Measure whitespace objective function value of CCPT on composite map.
7. Generate distribution of scores from CGT (point 6 a) and CCPT (point 6 f) and identify the solution which represents a compromising minimum in both distributions.
8. Calculate dose without modulation, and optimize the monitor unit distribution via simulated annealing using linear-quadratic penalty guided objective function.

Another example embodiment provides a method which computes dose matrices for each target at each control point, This step may be performed, for example by fitting a MLC conformally to each target volume taken alone. A cost function can then be used to quantify the relative contributions of each dose matrix in the plan to the overall plan objectives. Simulated annealing or an alternative optimization methods can then be performed to allow for the inclusion or exclusion of individual dose matrices at each control point. The exclusion of individual targets at a given control point may be accomplished by closing the MLC over the individual targets for durations determined by the simulated annealing or other optimization. Dynamic collimator motions may be employed to minimize the variation between the idealized dose matrices (i.e. perfectly collimated targets) and actual dose matrices (i.e. MLC apertures that include quantities of non-target tissue due to the relative orientations of targets in the field). An additional simulated annealing or other optimization may be performed to weight the relative contributions of dose at each control point (referred to as the monitor unit distribution (MUD)). MUD optimization may improve compliance with plan objectives.

Apparatus according to the invention may be configured to perform methods as described herein. The apparatus may, for example, comprise a radiation treatment planning system, an add-on module for a radiation treatment planning system, a radiotherapy system such as a linear accelerator, a control system for a radiotherapy system, or the like. Configuration of the apparatus may be provided by configuration information and/or instructions stored in a data store in or accessible to the apparatus and/or hardware design of the apparatus itself.

Figure 12:
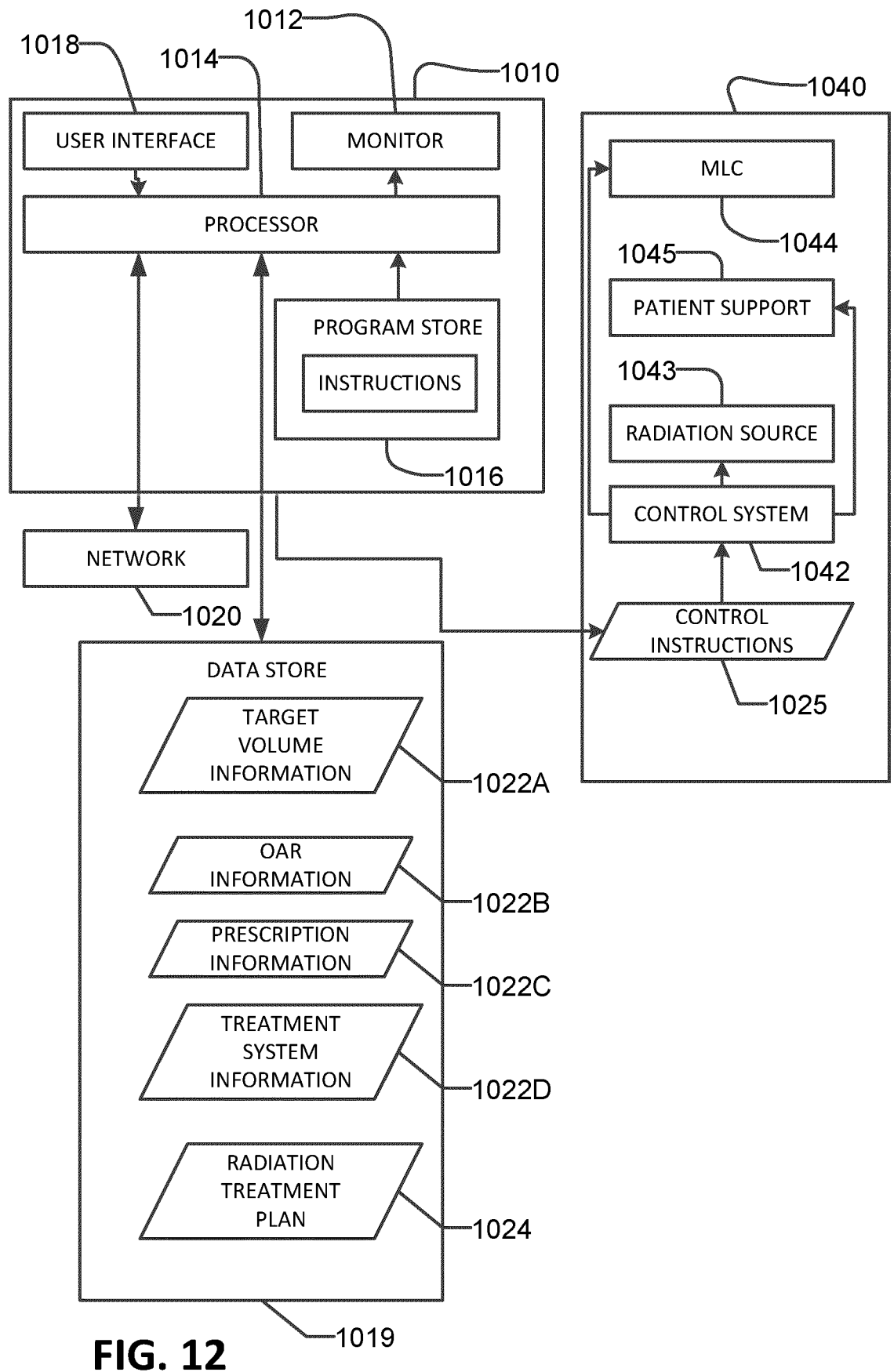
FIG. 12 is a block diagram of apparatus according to an example embodiment.

FIG. 12 shows apparatus 1000 according to an example embodiment. Apparatus 1000 includes a radiation treatment planning console 1010, comprising a monitor 1012, data processor 1014, program store containing instructions 1016 and user interface 1018. Radiation treatment planning console is connected to access input information for radiation treatment planning, for example, by way of a data communication network 1020, and/or input from user interface 1018, and/or from a local data store 1019, and/or from a connected radiation treatment system 1040. The input information may, for example, comprise:
target volume information 1022A defining the 3D configuration and location relative to a patient of target volumes;
prescription dose information 10228 specifying prescribed doses for the target volumes;
OAR information 1022C specifying the 3D configuration and location relative to a patient of one or more OARs;
treatment system information 1022D specifying the capabilities and configuration of treatment system 1040. The treatment system information may, for example, specify the configuration of a MLC or other beam shaper of treatment system 1040.

In some embodiments radiation treatment planning console 1010 is configured to derive one or more of the above types of information from other information (e.g. a set of planning imaging data) with or without guidance from a user.

Radiation treatment planning console 1010 generates a radiation treatment plan 1024. Plan 1024 may specify, for example, a trajectory for use in delivering a radiation treatment to a patient, beam shaper settings for locations along the trajectory and/or radiation beam settings for locations along the trajectory. Radiation treatment planning console 1010 may additionally generate control instructions 1025, which can be executed by a control system 1042 of radiation treatment system 1040 to implement the radiation treatment plan by delivering radiation to a patient according to plan 1024.

In the illustrated system 1000, radiation treatment system 1040 comprises a radiation source 1043 (e.g. a linear accelerator) equipped with a rotatable multileaf collimator 1044 and a positionable patient support 1045 such as an actuated couch.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, beam shaper, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for radiation treatment planning, the method comprising:
   for a plurality of target volumes each associated with a prescribed dose, wherein the prescribed doses are not all equal, determining shaping of an aperture for delivery of radiation from a radiation source at positions along a trajectory, the shaping selected to conform with boundaries of projections of the target volumes in a beam's eye view (BEV);
   selecting one or more of the target volumes for which the corresponding prescribed dose is less than a maximum of the prescribed doses, and,
   for each selected target volume determining the shaping without reference to the selected target volume for some portions of the trajectory;
   wherein determining the shaping comprises determining the shaping of the aperture for each of a plurality of control points spaced apart along the trajectory; and
   for each of one or more lower dose target volumes, wherein the lower dose target volumes are those of the target volumes excluding the target volume or target volumes associated with the maximum of the prescribed doses, establishing a quota of control points for which the lower dose target volume should be excluded from consideration in shaping the aperture based on a number of the control points for which the shaping of the aperture does not take into account the target volume or target volumes associated with a highest one of the prescribed doses; and
   for the one or more lower dose target volumes determining the shaping with reference to the target volume for some portions of the trajectory and determining the shaping without reference to the target volume for other portions of the trajectory according to the corresponding quota.

2. The method according to claim 1 wherein the shaping of the aperture for all of the control points takes into account the target volume or target volumes associated with the maximum of the prescribed doses.

3. The method according to claim 1 wherein the shaping of the aperture for at least some of the control points does not take into account the target volume or target volumes associated with the maximum of the prescribed doses.

4. The method according to claim 3 wherein the quotas for the lower dose target volumes are each set as a corresponding proportion of the number of the control points for which the shaping of the aperture does not take into account the target volume or target volumes associated with the maximum of the prescribed doses.

5. A method for radiation treatment planning, the method comprising:

for a plurality of target volumes each associated with a prescribed dose, wherein the prescribed doses are not all equal, determining shaping of an aperture for delivery of radiation from a radiation source at positions along a trajectory, the shaping selected to conform with boundaries of projections of the target volumes in a beam's eye view (BEV) wherein determining the shaping comprises determining the shaping of the aperture for each of a plurality of control points spaced apart along the trajectory; and performing a first optimization to determine a number of control points for which the shaping will be determined without reference to one or more of the target volumes for the one or more of the target volumes determining the shaping with reference to the target volume for some portions of the trajectory and determining the shaping without reference to the target volume for other portions of the trajectory according to the determined number of control points.

6. The method according to claim 5 further comprising performing a second optimization to select control points for which the shaping will be determined without reference to one or more of the target volumes.

7. The method according to claim 1 further comprising computing a blinking quota for one or more of the target volumes according to:

$$Q_{total,i} = CPT_{total} \cdot \left(1 - \left(\frac{Rx_i}{Rx_{max}}\right) \cdot \left(\frac{\overline{OF}_{max}}{\overline{OF}_i}\right)\right) \quad (1)$$

where i is an index for target volumes in a treatment plan, $Q_{total,i}$ is the number of control points to be blinked for the $i^{th}$ target volume, $CPT_{total}$ is the total number of control points, $Rx_i$ is the prescribed dose for the $i^{th}$ target volume, $Rx_{max}$ is the highest prescribed dose for any target volume found in the treatment plan, $\overline{OF}_{max}$ is the mean output factor for the target volume with the highest prescription dose, and $\overline{OF}_i$ is the mean output factor for the $i^{th}$ target volume.

8. The method according to claim 1 wherein, for each of the control points the method further comprises determining a configuration of movable elements of a beam shaper that fits the boundaries of the projections of the target volumes in the BEV.

9. A method for radiation treatment planning, the method comprising:

for a plurality of target volumes each associated with a prescribed dose, determining shaping of an aperture for delivery of radiation from a radiation source at positions along a trajectory, the shaping selected to conform with boundaries of projections of the target volumes in a beam's eye view (BEV) wherein determining the shaping comprises determining the shaping of the aperture for each of a plurality of control points spaced apart along the trajectory;

determining a quota for one or more of the target volumes, the quota specifying a number of the control points for which the shaping will be performed without reference to the corresponding target volume; and for the one or more of the target volumes determining the shaping with reference to the target volume for some portions of the trajectory and determining the shaping without reference to the target volume for other portions of the trajectory according to the quota.

10. The method according to claim 9 wherein the quota for a selected one of the target volumes is based at least in part on a ratio of the prescribed dose for the selected target volume to a maximum of the prescribed doses of the target volumes.

11. The method according to claim 10 wherein a proportion of the control points for which the selected one of the target volumes is excluded from consideration in shaping the aperture is set equal to or approximately equal to one minus the quotient of the prescribed dose for the selected target volume and the maximum prescribed dose.

12. The method according to claim 9 wherein the quota for a selected one of the target volumes is based in part on a comparison of an output factor for the selected target volume and an output factor for one of the target volumes corresponding to a maximum of the prescribed doses of the target volumes.

13. The method according to claim 12 wherein the output factor is determined for each target volume for each control point using calibration data which relates projected area in the BEV for the control point to the output factor.

14. The method according to claim 12 further comprising summing or averaging the output factors for a target volume over all of the control points.

15. The method according to claim 14 further comprising computing a ratio of total or average output factor for a target volume to the total or average output factor for a highest dose target volume for which the prescribed dose is equal to or exceeds the prescribed doses for all other ones of the treatment volumes.

16. A method for radiation treatment planning, the method comprising:

for a plurality of target volumes each associated with a prescribed dose, wherein the prescribed doses are not all equal, determining shaping of an aperture for delivery of radiation from a radiation source at positions along a trajectory, the shaping selected to conform with boundaries of projections of the target volumes in a beam's eye view (BEV); and, selecting one or more of the target volumes for which the corresponding prescribed dose is less than a maximum of the prescribed doses, and, for each selected target volume determining the shaping without reference to the selected target volume for some portions of the trajectory; and determining the shaping with reference to the selected target volume for some portions of the trajectory;

wherein the method further comprises determining average depths of one or more of the target volumes and basing a quota of control points for which the target volume should be excluded from consideration in shaping the aperture on the average depths.

17. The method according to claim 16 further comprising reducing the quota for target volumes having greater average depths relative to the quota for target volumes having smaller average depths.

18. The method according to claim 16 further comprising, for each selected target volume, identifying a set of the control points for which the shaping will be performed without reference to the selected target volume.

19. The method according to claim 18 wherein a number of the control points included in the set for the selected target volume is equal to the quota for the selected target volume.

20. The method according to claim 18 further comprising selecting the control points to be included in the set based on one or more of the following factors:

whether the projection of the target volume overlaps with projections of one or more other ones of the target volumes in the BEV for certain control points;

whether the projection of the target volume overlaps with, or is close to, projections of one or more organs at risk (OARs) for certain control points;

whether the configuration of the target volumes is such that for the BEV of certain control points a beam shaper being used cannot be readily configured to conform to boundaries of the projections of the target volumes.

21. The method according to claim 18 further comprising eliminating from consideration for inclusion in the set for a target volume those control points in which the projection of the target volume overlaps with a projection of another one of the target volumes.

22. The method according to claim 18 further comprising distributing the control points belonging to the set of control points approximately uniformly along the trajectory.

23. The method according to claim 18 wherein identifying the set of control points excludes from the set control points for which the projection of the selected target volume in the BEV overlaps with the projection of another target volume.

24. The method according to claim 18 wherein identifying the set of control points comprises identifying control points for which the projection of the selected target volume in the BEV overlaps with the projection of an organ at risk (OAR).

25. A method for radiation treatment planning, the method comprising:

for a plurality of target volumes each associated with a prescribed dose, wherein the prescribed doses are not all equal, determining shaping of an aperture for delivery of radiation from a radiation source at positions along a trajectory, the shaping selected to conform with boundaries of projections of the target volumes in a beam's eye view (BEV) wherein determining the shaping comprises determining the shaping of the aperture for each of a plurality of control points spaced apart along the trajectory; and, selecting one or more of the target volumes for which the corresponding prescribed dose is less than a maximum of the prescribed doses, and, for each selected target volume determining the shaping without reference to the selected target volume for some portions of the trajectory; and determining the shaping with reference to the selected target volume for some portions of the trajectory;

the method further comprising for each selected target volume, identifying a set of the control points for which the shaping will be performed without reference to the selected target volume and identifying the set of control points for the selected target volume comprises computing a blinking goal metric for each control point, the blinking goal metric indicative of a degree to which selecting that control point for inclusion in the set would satisfy a goal for distributing the control points belonging to the set.

26. The method according to claim 25 further comprising ranking the control points in order of the blinking goal metric and assigning the control points to the set for the corresponding selected target volume in the order until a quota for the corresponding target volume is satisfied.

27. A method for radiation treatment planning, the method comprising, for a plurality of target volumes each associated with a prescribed dose, wherein the prescribed doses are not all equal, determining shaping of an aperture for delivery of radiation from a radiation source at positions along a trajectory, the shaping selected to conform with boundaries of projections of the target volumes in a beam's eye view (BEV) wherein determining the shaping comprises determining the shaping of the aperture for each of a plurality of control points spaced apart along the trajectory; and, selecting one or more of the target volumes for which the corresponding prescribed dose is less than a maximum of the prescribed doses, and, for each selected target volume determining the shaping without reference to the selected target volume for some portions of the trajectory; and determining the shaping with reference to the selected target volume for some portions of the trajectory;

the method further comprising for at least one of the selected target volumes, identifying first and second sets of the control points for which the shaping will be performed without reference to the target volume, wherein identifying the first set comprises performing a first algorithm that permits clustering of control points in the first set and performing a second algorithm that is biased to providing a uniform distribution of the control points of the second set along the trajectory.

28. The method according to claim 1 wherein the beam shaper comprises a multileaf collimator.

29. The method according to claim 28 wherein the beam shaper configuration comprises both positions of leaves of the multileaf collimator and an angle of rotation of the multileaf collimator.

30. The method according to claim 28 wherein the multileaf collimator comprises first and second banks of movable leaves, and the method comprises positioning one of the movable leaves of the first bank of movable leaves to abut a corresponding one of the movable leaves of the second bank of movable leaves.

31. The method according to claim 30 further comprising optimizing locations of abutment of the abutting movable leaves.

32. The method according to claim 31 further comprising specifying locations of abutment of one or more sets of abutting movable leaves at adjacent control points.

33. The method according to claim 30 further comprising protecting non-target volumes from unnecessary radiation exposure by selecting a location of abutment of each of one or more sets of abutting movable leaves such that radiation leakage from the location of the abutment adds dose to a target volume.

34. The method according to claim 30 further comprising selecting a location of abutment of each of one or more sets of abutting movable leaves such that radiation leakage at the location of abutment occurs away from a projection of an organ at risk (OAR).

35. The method according to claim 1 wherein ratios of the extents of the portions of the trajectory for which the shaping is determined with reference to each of the target volumes are equal (to within 10%) to ratios of the prescribed doses corresponding to the target volumes.

36. The method according to claim 34 wherein the portions of the trajectory for which the shaping is determined without reference to the selected target volume are selected to avoid portions in which a projection of the target volume in the BEV overlaps with a projection of another target volume.

37. The method according to claim 35 wherein the portions of the trajectory for which the shaping is determined without reference to the selected target volume are selected to include portions of the trajectory in which a projection of the target volume in the BEV overlaps with a projection of an organ at risk (OAR).

38. The method according to claim 37 wherein the OAR comprises an eye, an optic nerve or a brainstem.

39. The method according to claim 1 further comprising receiving by way of a user interface commands which include one or more of:
- selecting one or more control points for which determining the shaping is required to be performed with reference to one or more of the target volumes;
- assigning to one or more control points one or more penalty values which cause a blink assignment algorithm to favour or disfavor allowing determining the shaping for the control point without reference to the target volume for one or more of the target volumes;
- manually causing the shaping to be determined without reference to a specific one of the target volumes for specific control points; and
- moving one or more of the control points on the trajectory.

40. The method according to claim 1 further comprising establishing the trajectory using 4π Optimization.

41. The method according to claim 1 wherein the trajectory comprises motion of a patient and motion of a radiation source.

42. The method according to claim 1 further comprising optimizing distribution of monitor units along the trajectory.

43. The method according to claim 1 further comprising performing an optimization of one more of:
- for each of the target volumes, for which parts of the trajectory is the target volume taken into consideration in the shaping or not taken into consideration in the shaping;
- for each of the target volumes, for what proportion of the trajectory is the target volume taken into consideration in the shaping;
- how are monitor units distributed along the trajectory; and
- how is the beam shaper configured at points along the trajectory.

44. The method according to claim 43 wherein performing the optimization comprises executing a simulated annealing algorithm.

45. The method according to claim 1 further comprising applying a whitespace measure to optimize the shaping of the aperture over the trajectory.

46. A non-transitory computer readable medium carrying machine readable instructions executable by a data processor, the machine-readable instructions, when executed, operative to cause the data processor to perform the method according to claim 1.

* * * * *